United States Patent
Ludwig et al.

(10) Patent No.: US 9,399,658 B2
(45) Date of Patent: Jul. 26, 2016

(54) PURIFICATION OF TRIPHOSPHORYLATED OLIGONUCLEOTIDES USING CAPTURE TAGS

(75) Inventors: Janos Ludwig, Goettingen (DE); Marion Goldeck, Bonn (DE); Brian Sproat, Booischot (BE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 0 days.

(21) Appl. No.: 14/007,752

(22) PCT Filed: Mar. 28, 2012

(86) PCT No.: PCT/EP2012/055520
§ 371 (c)(1),
(2), (4) Date: Sep. 26, 2013

(87) PCT Pub. No.: WO2012/130886
PCT Pub. Date: Oct. 4, 2012

(65) Prior Publication Data
US 2014/0024819 A1    Jan. 23, 2014

(30) Foreign Application Priority Data
Mar. 28, 2011 (EP) .................................. 11160032

(51) Int. Cl.
C07H 21/00 (2006.01)
C07H 21/02 (2006.01)
C07H 1/04 (2006.01)

(52) U.S. Cl.
CPC .................. *C07H 21/02* (2013.01); *C07H 1/04* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 3,534,017 A | 10/1970 | Fujimoto et al. | |
| 4,210,746 A | 7/1980 | Kerr et al. | |
| 4,522,811 A | 6/1985 | Eppstein et al. | |
| 5,166,195 A | 11/1992 | Ecker | |
| 5,194,428 A | 3/1993 | Agrawal et al. | |
| 5,264,423 A | 11/1993 | Cohen et al. | |
| 5,271,941 A | 12/1993 | Cho-Chung | |
| 5,292,875 A | 3/1994 | Stec et al. | |
| 5,366,878 A | 11/1994 | Pederson et al. | |
| 5,606,049 A | 2/1997 | Vaghefi | |
| 5,635,377 A | 6/1997 | Pederson et al. | |
| 5,644,048 A | 7/1997 | Yau | |
| 5,646,267 A | 7/1997 | Stec et al. | |
| 5,652,355 A | 7/1997 | Metelev et al. | |
| 5,736,294 A | 4/1998 | Ecker et al. | |
| 5,770,713 A | 6/1998 | Imbach et al. | |
| 6,143,881 A | 11/2000 | Metelev et al. | |
| 6,344,323 B1 | 2/2002 | Seifert | |
| 6,346,614 B1 | 2/2002 | Metelev et al. | |
| 6,369,209 B1 | 4/2002 | Manoharan et al. | |
| 6,737,520 B2 | 5/2004 | Manoharan et al. | |
| 6,900,308 B2 | 5/2005 | Wyrzykiewicz et al. | |
| 7,119,184 B2 | 10/2006 | Manoharan et al. | |
| 7,217,807 B2 | 5/2007 | Bentwich | |
| 7,285,658 B2 | 10/2007 | Cook et al. | |
| 7,371,735 B2 | 5/2008 | Harel-Bellan et al. | |
| 7,598,230 B2 | 10/2009 | Cook et al. | |
| 7,696,334 B1 | 4/2010 | Bentwich | |
| 7,696,342 B1 | 4/2010 | Bentwich | |
| 7,759,478 B1 | 7/2010 | Bentwich | |
| 7,790,867 B2 | 9/2010 | Bentwich | |
| 7,807,653 B2 | 10/2010 | Cook et al. | |
| 7,862,816 B2 | 1/2011 | Krasnoperov et al. | |
| 8,563,709 B2 | 10/2013 | Iba et al. | |
| 8,912,158 B2 | 12/2014 | Dimmeler et al. | |
| 2008/0664786 | 6/1996 | Agrawal | |
| 2003/0129615 A1 | 7/2003 | Wyrzykiewicz et al. | |
| 2003/0171570 A1 | 9/2003 | Schweitzer | |
| 2003/0203868 A1 | 10/2003 | Bushman | |
| 2004/0059104 A1 | 3/2004 | Cook et al. | |
| 2004/0234999 A1 | 11/2004 | Farrar et al. | |
| 2004/0261149 A1 | 12/2004 | Fauquet et al. | |
| 2005/0026861 A1 | 2/2005 | Kandimalla et al. | |
| 2005/0182005 A1 | 8/2005 | Tuschl et al. | |
| 2005/0222060 A1 | 10/2005 | Bot et al. | |
| 2005/0249736 A1 | 11/2005 | Krasnoperov et al. | |
| 2006/0035815 A1 | 2/2006 | Chen et al. | |
| 2006/0178334 A1 | 8/2006 | Rossi et al. | |
| 2007/0066521 A1 | 3/2007 | Fauquet | |
| 2007/0259832 A1 | 11/2007 | Cook et al. | |
| 2007/0265220 A1 | 11/2007 | Rossi et al. | |
| 2007/0265224 A1 | 11/2007 | Cook et al. | |
| 2007/0287681 A1 | 12/2007 | Jeong et al. | |
| 2008/0171712 A1 | 7/2008 | Kandimalla et al. | |
| 2008/0188428 A1 | 8/2008 | Bentwich | |
| 2008/0250532 A1 | 10/2008 | Abdullah et al. | |
| 2009/0143327 A1 | 6/2009 | Smolke et al. | |

(Continued)

FOREIGN PATENT DOCUMENTS

| | | |
|---|---|---|
| CN | 1434054 A | 8/2003 |
| CN | 101088565 A | 12/2007 |

(Continued)

OTHER PUBLICATIONS

Wang et al. J. Med. Chem. (2004), vol. 47, pp. 6902-6913.*

(Continued)

*Primary Examiner* — Patrick Lewis
(74) *Attorney, Agent, or Firm* — Rothwell, Figg, Ernst & Manbeck, P.C.

(57) ABSTRACT

The present invention relates to a method of preparing triphosphate-modified oligonucleotides using a capture tag. The method allows the synthesis and purification of triphosphate-modified oligonucleotides in high yield and purity suitable for pharmaceutical applications.

18 Claims, 22 Drawing Sheets

(56) References Cited

U.S. PATENT DOCUMENTS

| | | |
|---|---|---|
| 2009/0203121 A1 | 8/2009 | Hochberg et al. |
| 2009/0203894 A1 | 8/2009 | Liu et al. |
| 2010/0178272 A1 | 7/2010 | Hartmann |
| 2010/0260788 A1 | 10/2010 | Debelak et al. |
| 2010/0303859 A1 | 12/2010 | Williams |
| 2011/0130738 A1 | 6/2011 | Schmidt |
| 2011/0165133 A1 | 7/2011 | Rabinovich et al. |
| 2011/0245481 A1 | 10/2011 | Iba et al. |
| 2011/0247091 A1 | 10/2011 | Magor et al. |
| 2012/0225924 A1 | 9/2012 | Lin et al. |
| 2013/0121989 A1 | 5/2013 | Gaertig et al. |
| 2013/0189367 A1 | 7/2013 | Zhang et al. |
| 2013/0302252 A1 | 11/2013 | Zhang et al. |
| 2014/0171368 A1 | 6/2014 | Goepferich et al. |
| 2015/0018407 A1 | 1/2015 | Dimmeler et al. |

FOREIGN PATENT DOCUMENTS

| | | |
|---|---|---|
| CN | 101190944 A | 6/2008 |
| CN | 101632833 A | 1/2010 |
| CN | 101974529 A | 2/2011 |
| CN | 102475892 A | 5/2012 |
| DE | 1 695 303 A | 4/1972 |
| DE | 41 10 085 A1 | 10/1992 |
| DE | 10 2007 052 114 A1 | 5/2009 |
| EP | 0 021 099 A1 | 1/1981 |
| EP | 0 031 285 A2 | 7/1981 |
| EP | 0 043 075 A2 | 1/1982 |
| EP | 0 081 099 A2 | 6/1983 |
| EP | 0 339 842 A2 | 11/1989 |
| EP | 0 386 563 A1 | 9/1990 |
| EP | 0 415 901 A2 | 3/1991 |
| EP | 0 698 034 B1 | 2/1996 |
| EP | 0 754 188 B1 | 11/1997 |
| EP | 0 788 366 B1 | 12/1999 |
| EP | 0 739 899 B1 | 6/2001 |
| EP | 1 247 815 A2 | 10/2002 |
| EP | 1 493 818 A2 | 1/2005 |
| EP | 1 505 152 A1 | 2/2005 |
| EP | 1 626 086 A2 | 2/2006 |
| EP | 1 637 597 A1 | 3/2006 |
| EP | 1 657 306 A1 | 5/2006 |
| EP | 1 743 901 A2 | 1/2007 |
| EP | 5020019.5 A1 | 3/2007 |
| EP | 5020020.3 A1 | 3/2007 |
| EP | 05 020 019.5 A1 | 12/2007 |
| EP | 05 020 020.3 A1 | 12/2007 |
| EP | 06 016 578.4 A2 | 12/2007 |
| EP | 6016578.4 A1 | 2/2008 |
| EP | 1 939 291 A2 | 7/2008 |
| EP | 2 113 565 A1 | 11/2009 |
| EP | 2 141 234 A1 | 1/2010 |
| EP | 2 207 797 A1 | 7/2010 |
| EP | 1 453 962 B1 | 8/2010 |
| EP | 2 213 738 A2 | 8/2010 |
| EP | 2 284 266 A2 | 2/2011 |
| EP | 2 327 783 A1 | 6/2011 |
| EP | 2 338 449 A1 | 6/2011 |
| EP | 2 338 499 A1 | 6/2011 |
| EP | 1 857 119 B1 | 11/2011 |
| EP | 2 277 508 B1 | 4/2012 |
| EP | 1 969 125 B1 | 6/2012 |
| EP | 2 497 827 A1 | 9/2012 |
| EP | 2 123 757 B1 | 10/2012 |
| EP | 2 508 530 A1 | 10/2012 |
| EP | 2 514 758 A1 | 10/2012 |
| EP | 2 518 150 A2 | 10/2012 |
| EP | 1 920 775 B1 | 12/2012 |
| EP | 2 551 354 A1 | 1/2013 |
| EP | 1 915 448 B1 | 9/2013 |
| EP | 2 671 949 A1 | 12/2013 |
| EP | 1 957 648 B1 | 4/2014 |
| EP | 1 973 574 B1 | 4/2014 |
| EP | 2 712 870 A1 | 4/2014 |
| EP | 2 069 500 B1 | 9/2014 |
| EP | 2 207 787 B1 | 11/2014 |
| EP | 2 492 355 B1 | 4/2015 |
| JP | 0H6-501843 A | 3/1994 |
| JP | H6-501843 A | 3/1994 |
| JP | 07-099976 A | 4/1995 |
| JP | 08-154687 A | 6/1996 |
| JP | 2003-535043 A | 11/2003 |
| JP | 2005-526778 A | 9/2005 |
| JP | 2006-238795 A | 9/2006 |
| WO | WO 84/00688 A1 | 3/1984 |
| WO | WO 89/08146 A1 | 9/1989 |
| WO | WO 90/14353 A1 | 11/1990 |
| WO | WO 91/06309 A1 | 5/1991 |
| WO | WO 92/02641 A1 | 2/1992 |
| WO | WO 92/03454 A1 | 3/1992 |
| WO | WO 92/17484 A1 | 10/1992 |
| WO | WO 93/07882 A1 | 4/1993 |
| WO | WO 93/08296 A1 | 4/1993 |
| WO | WO 93/23569 A1 | 11/1993 |
| WO | WO 94/02501 A1 | 2/1994 |
| WO | WO 94/15619 A1 | 7/1994 |
| WO | WO 94/17093 A1 | 8/1994 |
| WO | WO 94/24144 A2 | 10/1994 |
| WO | WO 94/26764 A1 | 11/1994 |
| WO | WO 95/03406 A2 | 2/1995 |
| WO | WO 95/32719 A1 | 12/1995 |
| WO | WO 96/02556 A2 | 2/1996 |
| WO | WO 96/07392 A2 | 3/1996 |
| WO | WO 96/18736 A1 | 6/1996 |
| WO | WO 96/19572 A1 | 6/1996 |
| WO | 9640159 A1 | 12/1996 |
| WO | WO 96/40159 A1 | 12/1996 |
| WO | WO 96/41812 B1 | 12/1996 |
| WO | WO 99/55857 A2 | 11/1999 |
| WO | WO 00/66609 A1 | 11/2000 |
| WO | WO 01/16312 A2 | 3/2001 |
| WO | WO 01/22990 A2 | 5/2001 |
| WO | WO 01/68077 A2 | 9/2001 |
| WO | WO 01/70751 A1 | 9/2001 |
| WO | WO 02/10432 A2 | 2/2002 |
| WO | WO 03/008432 A1 | 1/2003 |
| WO | WO 03/012052 A2 | 2/2003 |
| WO | WO 03/072757 A2 | 9/2003 |
| WO | WO 03/078595 A2 | 9/2003 |
| WO | WO 03072575 | 9/2003 |
| WO | WO 03/086280 | 10/2003 |
| WO | WO 03/086280 A2 | 10/2003 |
| WO | WO 03/087367 A2 | 10/2003 |
| WO | WO 03/087368 A2 | 10/2003 |
| WO | WO 03/101375 | 12/2003 |
| WO | WO 03/101375 A2 | 12/2003 |
| WO | WO 2004/015062 A2 | 2/2004 |
| WO | WO 2004/020631 A2 | 3/2004 |
| WO | WO 2004/022777 A1 | 3/2004 |
| WO | WO 2004/024063 A2 | 3/2004 |
| WO | WO 2004/044123 A2 | 5/2004 |
| WO | WO 2004/045543 A2 | 6/2004 |
| WO | WO 2004/048511 A2 | 6/2004 |
| WO | WO 2004/061423 A2 | 7/2004 |
| WO | WO 2004/074441 A2 | 9/2004 |
| WO | WO 2004/080418 A2 | 9/2004 |
| WO | WO 2004/080425 A2 | 9/2004 |
| WO | WO 2004/083430 A2 | 9/2004 |
| WO | WO 2004/085623 A2 | 10/2004 |
| WO | WO 2004/106517 A1 | 12/2004 |
| WO | WO 2004/111190 A2 | 12/2004 |
| WO | WO 2005/005632 A2 | 1/2005 |
| WO | WO 2005/076979 A2 | 8/2005 |
| WO | WO 2005/089287 A2 | 9/2005 |
| WO | WO 2005/108573 A2 | 11/2005 |
| WO | WO 2005/117991 A2 | 12/2005 |
| WO | WO 2006/016574 A1 | 2/2006 |
| WO | WO 2006/063252 A2 | 6/2006 |
| WO | WO 2006/074400 A2 | 7/2006 |
| WO | WO 2006/078646 A2 | 7/2006 |
| WO | WO 2006/105361 A2 | 10/2006 |
| WO | WO 2006/110813 A2 | 10/2006 |
| WO | WO 2006/119643 A1 | 11/2006 |

(56) References Cited

FOREIGN PATENT DOCUMENTS

| WO | WO 2006/122409 A1 | 11/2006 |
|---|---|---|
| WO | WO 2006/128739 A1 | 12/2006 |
| WO | WO 2006/130949 A1 | 12/2006 |
| WO | WO 2007/021142 A1 | 2/2007 |
| WO | WO 2007/030619 A2 | 3/2007 |
| WO | WO 2007/031319 A1 | 3/2007 |
| WO | WO 2007/031322 | 3/2007 |
| WO | WO 2007/038788 A2 | 4/2007 |
| WO | WO 2007/051303 A1 | 5/2007 |
| WO | WO 2007/107304 A2 | 9/2007 |
| WO | WO 2008/017473 A2 | 2/2008 |
| WO | WO 2008/045576 A2 | 4/2008 |
| WO | WO 2008/076127 A1 | 6/2008 |
| WO | WO 2008/080091 A2 | 7/2008 |
| WO | WO 2008/087641 A2 | 7/2008 |
| WO | WO 2008/087642 A2 | 7/2008 |
| WO | WO 2008/099396 A1 | 8/2008 |
| WO | WO 2008/124165 A2 | 10/2008 |
| WO | WO 2008/131807 A2 | 11/2008 |
| WO | WO 2008/134593 A1 | 11/2008 |
| WO | WO 2009/018500 A1 | 2/2009 |
| WO | WO 2009/038707 A2 | 3/2009 |
| WO | WO 2009/046541 A1 | 4/2009 |
| WO | WO 2009/051659 A1 | 4/2009 |
| WO | 2009060281 A2 | 5/2009 |
| WO | WO 2009/056116 A1 | 5/2009 |
| WO | WO 2009/060124 A2 | 5/2009 |
| WO | WO 2009/060281 A2 | 5/2009 |
| WO | WO 2009/061417 A1 | 5/2009 |
| WO | WO 2009/064590 A2 | 5/2009 |
| WO | WO 2009/068677 A1 | 6/2009 |
| WO | WO 2009/083738 A2 | 7/2009 |
| WO | WO 2009/141146 A1 | 11/2009 |
| WO | WO 2009/146556 A1 | 12/2009 |
| WO | WO 2009/151600 A2 | 12/2009 |
| WO | WO 2010/028079 A2 | 3/2010 |
| WO | WO 2010/042742 A2 | 4/2010 |
| WO | WO 2010/042749 A2 | 4/2010 |
| WO | WO 2010/042751 A2 | 4/2010 |
| WO | WO 2010/042755 A2 | 4/2010 |
| WO | WO 2010/047216 A1 | 4/2010 |
| WO | WO 2010/062502 A1 | 6/2010 |
| WO | WO 2010/099161 A1 | 9/2010 |
| WO | WO 2010/118263 A1 | 10/2010 |
| WO | WO 2010/120874 A2 | 10/2010 |
| WO | WO 2010/136192 A1 | 12/2010 |
| WO | WO 2010/147655 A2 | 12/2010 |
| WO | WO 2011/008857 A1 | 1/2011 |
| WO | WO 2011/011716 A1 | 1/2011 |
| WO | 2011028218 A1 | 3/2011 |
| WO | WO 2011/028218 A1 | 3/2011 |
| WO | WO 2011/064130 A1 | 6/2011 |
| WO | WO 2011/133559 A2 | 10/2011 |
| WO | WO 2011/138328 A2 | 11/2011 |
| WO | WO 2011/140285 A2 | 11/2011 |
| WO | WO 2012/056449 A2 | 5/2012 |
| WO | WO 2012/056457 A2 | 5/2012 |
| WO | WO 2012/091523 A2 | 7/2012 |
| WO | WO 2012/125987 A2 | 9/2012 |
| WO | WO 2012/130886 A1 | 10/2012 |
| WO | WO 2013/003887 A1 | 1/2013 |
| WO | WO 2013/013820 A1 | 1/2013 |
| WO | WO 2013/020986 A1 | 2/2013 |
| WO | WO 2013/053480 A1 | 4/2013 |
| WO | WO 2013/053481 A1 | 4/2013 |
| WO | WO 2013/075140 A1 | 5/2013 |
| WO | WO 2013/153082 A1 | 10/2013 |
| WO | WO 2014/049079 A1 | 4/2014 |
| WO | WO 2014/124433 A1 | 8/2014 |

OTHER PUBLICATIONS

Ludwig et al. J. Org. Chem. (1989), vol. 54, pp. 631-635.*
Lebedev A V et al: "Preparation of Oligodeoxynucleotide 5' Triphosphates Using Solid Support Approach",Nucleosides, Nucleotides and Nucleic Acids, Taylor & Francis, Philadelphia, PA, vol. 20, No. 4-7, Jan. 1, 2001, pp. 1403-1409, XP009081 703,ISSN: 1525-7770, DOI: 10.1081/NCN-100002565.
Martin Schlee et al: "Recognition of 5' Triphosphate by RIG-I Helicase Requires Short Blunt Double-Stranded RNA as Contained in Panhandle of Negative-Strand Virus",Immunity, vol. 31, No. 1, Jul. 17, 2009, pp. 25-34, XP55032801,ISSN: 1074-7613, DOI: 10.1016/j.immuni.2009.05.008.
Ivan Zlatev et al: "Efficient Solid-Phase Chemical Synthesis of 5'-Triphosphates of DNA, RNA, and their Analogues", Organic Letters, vol. 12, No. 10, May 21, 2010, pp. 2190-2193, XP055005331, ISSN: 1523-7060, DOI: 10.1021/ol1004214.
Gaur et al., "Novel Solid PHase Synthesis of 2'-o-Methylribonucleoside 5'-Triphosphates and Their α-Thio Analogues", Tetrahedron Letters, vol. 33, No. 23, pp. 3301-3304, 1992.
Sproat et al., "Fast and simple purification of chemically modified hammerhead ribozymes using a lipophilic capture tag", Nucleic Acids Research, 1999, vol. 27, No. 8.
Absher, et al., *Nature* 223:715-717 (Aug. 16, 1969).
Adam, et al., *Blood*, 106(1):338-344 (2005).
Adelfinskaya, et al., *Angew. Chem. Int. Ed.*, 46:4356-4358 (2007).
Adelfinskaya, et al., *Nucleic Acids Research*, 35(15):5060-5072 (2007).
Aigner, et al., *J. Biomed. Biotechnol*.2006(4):71659 (2006).
Akira, et al., *C R Biol*. 327(6):581-9 (2004).
Aleman, et al., *RNA* 13(3):385-395 (Mar. 2007).
Alexopoulou, et al., *Nature*, 413(6857):732-8 (2001).
Ambion, Life Technologies Corporation, Catalog Nos. AM 1330, AM1333, AM1334, AM1338, Publ. No. 1330M, Revision G. (2012).
Andrejeva, et al., *Proc Natl Acad Se*; USA, 101:17264-9 (Dec. 7, 2004).
Arnold, et al., *J.Biol.Chem.*, 274(5):1706-2716 (1999).
Barton, et al., *Nat Immunol* 7:49-56 (Jan. 2006).
Bartonschlager, et al., *J. Gen. Virol.*,81:1631-1648 (2000).
Bass, et al., *Cell* 55(6):1089-98 (1988).
Baudin, et al., *EMBO J.*,13(13):3158-3166 (1994).
Behlke, et al., *Mol Ther*, 13(4):644-670 (Apr. 2006).
Bekeredjian-Ding, et al., *J Immunol*,174: 4043-50 (Apr. 1, 2005).
Besch, et al., *Cell Death Differ*, 14:818-29 (2007).
Blackburn, et al., *J.C.S. Chem. Commun.*, 1188-1190 (1981).
Blumberg, et al., *Cell*, 23(3):837-45 (Mar. 1981).
Blumberg, et al., *J Virol.*, 40(2):568-76 (Nov. 1981).
Bonin, et al., *RNA*, 6:563-570 (2000).
Bowie, et al., *Trends in Immunology*, 28(4):147-150 (2007).
Brownlee, et al., *Nucleic Acids Research*, 23(14):2641-2647 (1995).
Brzozka, et al. *Journal of Virology*, 80:2675-83 (Mar. 2006).
Brzozka, et al., *Journal of Virology*, 79:7673-81 (Jun. 2005).
Bui, et al., *Curr. Opin. Immunol.*, 19:203-8 (2007).
CA 2589406; Alnylam Pharmaceuticals, Inc.; Publ. Jun. 15, 2006.
Carroll, et al. *Methods in Enzymology*, 275:365-382 (1996).
Cazenave, et al., *Proc. Natl. Acad. Sci. USA*, 91:6672-6976 (1994).
Chang et al., *Microbes and Infection* 8, 157 (2006).
Chaperot, et al., *The Journal of Immunology*, 176:248-255 (2006).
Chawla-Sarkar, et al., *Cell Death and Differentiation*, 11:915-923 (2004).
Chemicool, "Definition of Homogeneous," in *Chemicool* (2014). Retrieved on Jan. 25, 2015 from www.chemicool.com/definition/homogeneous.html.
Chen, et al., *J Virol.*, 81(2):964-76 (2007).
Cheong, et al., *Nucleic Acids Res*, 24(21):4197-4201 (D35) (1996).
Chien, et al., *Cancer Gene Therapy*, 12(3):321-328 (2005).
Chiocca, *Nat Rev Cancer*, 2:938-950 (2002).
Coe, et al., *J. Chem. Soc., Chem. Commun.*, 312-314 (1991).
Coffey, et al., *Science*, 282:1332-1334 (1998).
Colonno, et al., *Cell*, 15:93-101 (1978).
Cuesta, *J Immunol.*, 178(6):3602-11 (2007).
Cui, et al. *Molecular Cell*, 29:169-179 (2008).
Cullen, *Mol Cell*, 16:861-5 (Dec. 22, 2004).
Curiel, *J. Clin. Invest.*, 117:1167-74 (2007).
Danial, et al., *Cell*, 116:205-19 (2004).
Davis, et al., *PNAS*, 101(29):10697-10702 (Jul. 20, 2004).
De Fougerolles, et al., *J. Nat.Rev.Drug Discov.*, 6:443-53 (2007).
De Jonge, et al., *Gene Therapy*, 13:400-411 (2006)).

(56) References Cited

OTHER PUBLICATIONS

Decatur, et al., *J. Biol. Chem.*, 278:695-8 (Jan. 3, 2003).
Delale, et al., *J Immunol*, 175:6723-32 (Nov. 15, 2005).
Der, et al, *Proc Natl Acad Sci USA*, 92:8841-5 (Sep. 12, 1995).
Diebold, et al., *Nature*, 424:324-8 (Jul. 17, 2003).
Diebold, et al., *Science*, 303:1529-31 (Mar. 5, 2004).
Duan, et al., *Antiviral Therapy*, 13(1):109-114 (2008).
Dunn, et al., *J Mol Biol*, 166:477-535 (Jun. 5, 1983).
Elbashir, et al., *Nature*, 411:494-498 (May 24, 2001).
Elbashir, et al., *The EMBO Journal*, 20(23):6877-6888 (2001).
Entry "influenca A virus" in Wikipedia.
Entry "Oligonucleotide synthesis" in Wikipedia.
Fromont-Racine, et al., *Gene*, 313:17-42 (Aug. 14, 2003).
Furuichi, et al., *Adv Virus Res*, 55:135-84 (2000).
Gaur, et al., *Tetrahedron Letters*, 33:3301-3304 (1992).
GenBank Acc No. AF389115.1 (Sep. 19, 2002) Influenza A virus (A/Puerto Rico/8/34/Mount Sinai (H1N1, segment 1, complete sequence (see first nucleotide, Pos. 1) (D15).
GenBank Acc No. AF389116.1 (Sep. 19, 2002) Influenza A virus (A/Puerto Rico/8/34/Mount Sinai (H1N1)), segment 2, complete sequence (see first nucleotide, Pos. 1) (D16).
GenBank Acc No. AF389117.1 (Sep. 19, 2002) Influenza A virus (A/Puerto Rico/8/34/Mount Sinai (H1N1)), segment 3, complete sequence (see first nucleotide, Pos. 1) (D17).
GenBank Acc No. AF389118.1 (Sep. 19, 2002) Influenza A virus (A/Puerto Rico/8/34/Mount Sinai (H1N1)), segment 4, complete sequence (see first nucleotide, Pos. 1) (D18).
GenBank Acc No. AF389119.1 (Sep. 19, 2002) Influenza A virus (A/Puerto Rico/8/34/Mount Sinai (H1N1)), segment 5, complete sequence (see first nucleotide, Pos. 1) (D19).
GenBank Acc No. AF389120.1 (Sep. 19, 2002) Influenza A virus (A/Puerto Rico/8/34/Mount Sinai (H1N1)), segment 6, complete sequence (see first nucleotide, Pos. 1) (D20).
GenBank Acc No. AF389121.1 (Sep. 19, 2002) Influenza A virus (A/Puerto Rico/8/34/Mount Sinai (H1N1)), segment 7, complete sequence (see first nucleotide, Pos. 1) (D21).
GenBank Acc No. AF389122.1 (Sep. 19, 2002) Influenza A virus (A/Puerto Rico/8/34/Mount Sinai (H1N1)), segment 8, complete sequence (see first nucleotide, Pos. 1) (D22).
GenBank Acc. No. AF221499.1 (Mar. 9, 2001) Japanese encephalitis virus, isolate CH2195LA, complete genome (see first nucleotide, Pos. 1) (D14).
GenBank Acc. No. J02428.1 (Oct. 21, 2002) Vesicular stomatitis Indiana virus, complete genome (see first nucleotide, Pos. 1) (D13).
Gerber, et al., *Trends Biochem Sci*, 26(6):376-84 (2001).
Gerrits, digital dissertation, FU Berlin, 2001, English Abstract.
Gitlin, et al., *Proc Natl Acad Sci USA*, 103(22):8459-64 (2006).
Goldeck, et al., *Angew. Chem.*, 126(4):782-786 (2014).
Gondai, et al., *Nucleic Acids Res*, 36(3):e18 (2008).
Grzelinski, et al., *Hum Gene Ther.*, 17(7):751-66 (2005).
Haas, et al., *Immunity*, 28:315-232 (2008).
Hanahan, et al., *Cell*, 100:57-70 (2000).
Hartmann, et al., *Handbook of RNA Biochemistry*, pp. 6, 39, 43 (2005).
Heil, et al., *Science*, 303:526-9 (Mar. 5, 2004).
Helm, et al., *RNA*, 1999, vol. 5, p. 618-621.
Hemmi, et al., *Nat Immunol*, 3:196 (Feb. 2002).
Hemmi, et al., *Nature*, 408:740-5 (Dec. 7, 2000).
Henry, et al., *J Exp Med* 204(5):987-94 (2007).
Hofacker, et al., *Bioinformatics*, 20:1495-1499 (2004).
Holý, et al., *Collect. Czech. Commun.*, 47:3447-3463 (1982).
Honda, et al., *Virus Res*, 55: 199-206 (Jun. 1998).
Hornung, et al., *J Immunol*, 168:4531-7 (May 1, 2002).
Hornung, et al., *Nat Med*, 11(3):263-70 (Mar. 2005).
Hornung, et al. *Science*, 314:994-7 (2006).
Hsu, et al., *Croc.Natl.Acad.Sci.U.S.A.*, 84:8140-8141 (1987).
Huang, et al., *Biochemistry*, 39 (50):15548-15555 (2000).
Ishii, et al., *Nat Immunol*, 7:40-8 (Jan. 2006).
Jiang, et al., *Genes & Dev*, 17:832-837 (2003).
Judge, et al., *Nat Biotechnol*, 23:457-462 (2005).

Kamphuis, et al., *Blood*, 108:3253-61 (2006).
Kanneganti, et al. *Nature*, 440 (7081):233-6 (2006).
Kao, et al., *Virology*, 287:251-260 (2001).
Kariko, et al., *Biochem. Biophys. Res. Commun.*, 128(2):695-698 (1985).
Kariko, et al., *Immunity*, 23:165-75 (Aug. 2005).
Kato, et al., *Immunity*, 23(1):19-28 (Jul. 2005).
Kato, et al., *Nature*, 441 (7089):101-105 (Apr. 9, 2006).
Kawai, et al., *Nat Immunol*, 6(10):981-988 (Oct. 2005).
Kawai, et al., *Nat Immunol*, 7(2):131-7 (2006).
Kennedy, et al., *J.Mol.Biol.*, 370:256-268 (2007).
Khan, et al., *J Drug Target*, 12(6):393-404 (2004).
Kim, et al., *Nat Biotechnol*, 22:321-325 (Mar. 2004).
Knorre, et al., *FEBS Letters*, 70(1):105-108 (1976).
Koh, et al., *J. Med. Chem.*, 48:2867-2875 (2005).
Kossen, et al. *Chemistry and Biology*, 11:807-815 (2004).
Krieg, *Annu Rev Immunol*, 20:709-60 (2002).
Krieg, et al., *Nature*, 374:546-9 (Apr. 6, 1995).
Krug, et al., *Eur J Immunol*, 31:2154-63 (Jul. 2001).
Krug, et al., *Immunity*, 21:107-19 (Jul. 2004).
Krupp, *Gene*, 72:75-89 (1988).
Kuzmine, et al., *The Journal of Biol. Chem.*, 278(5):2819-2823 (2003).
Latz, et al., *Nat Immunol*, 5 (2):190-8 (2004).
Latz, et al., *Nat. Immunol*, 8:772-779 (2007).
Lau, et al. *J Exp Med*, 202 (9):1171-7 (2005).
Lebedev, et al., *Nucleosides, Nucleotides and Nucleic Acids*, 20(4-7):1403-1409 (2001).
Lee, et al., Proc Natl Acad Sci USA, 74:59-63 (Jan. 1977).
Limbach, et al., *Nucleic Acids Res*, 22:2183-2196 (1994).
Loo, et al., *J Virol*, 82:335-345 (2008).
Lu, et al., *Nucleic Acids Res*, 39(4):1565-1575 (Mar. 2011).
Ludwig, *Acta Biochim Biophys Acad Sci Hung*, 16:131-3 (1981).
Ludwig, et al., *J. Org Chem.*, 54:631-635 (1989).
Ludwig, et al., *J. Org. Chem.*, 56:1777-1783-D9 (1991).
Ma, et al., *Molecular Therapy—Nucleic Acids*, 3(e161):1-11 (2014).
Maitra, et al., *PNAS*, 77(7):3908-3911 (1980).
Marques, et al., *Nat Biotechnol*, 24(5):559-565 (May 2006).
Matsumoto, et al., *J Immunol*, 171(6):3154-62 (2003).
McHill, et al., *Cell*, 109:707-18 (2002).
Meister, et al., *Mol Cell*, 15:185 (Jul. 23, 2004).
Melchjorsen, et al., *J Virol*, 79:12944-51 (2005).
Meyer, et al., *Methods in Molecular Biol*, 1086:21-40 (2014).
Meylan, et al., *Nature*, 437(7062):1167-72 (Oct. 20, 2005).
Miller, et al., *N.Engl.J.Med.* 355:51-65 (2006).
Milligan, et al., *Dep. of Chem. And Biochem.*, 15(21):8783-98 (1987).
Milligan, et al., *Methods in Enzymology, RNA Processing, Part A General Methods*, p. 51-62 (1989).
Minakuchi, et al., *Nucleic Acids Research*, 32(13):e109 (2004).
Mocikat, et al., *Immunity*, 19:516-569 (Oct. 2003).
Muller, et al., *Science*, 264:1918-21 (1994).
Neumann, et al., *Curr. Topics in•Microbiol. and Immunol.*, 283:121-43 (2004).
Nishiya, et al, *J Biol Chem*, 279(18):19008-17 (2004).
Obeid, et al., *Nat.Med.*, 13:54-61 (2007).
Olsen, et al., *Journal of Biological Chemistry*, 271(13):7435-7439 (1996).
Palladino, et al., *Cell*, 102(4):437-49 (2000).
Paul, et al. *Chemistry and Biology*, 13:329-338 (2006).
Pearse, et al., *Adv Drug Deliv Rev*, 57(3):465-474 (Jan. 10, 2005).
Pei et al., *Nat. Methods*, 3:670-6 (2006).
Peterli, et al., *Helvetica Chimica Acta*, 75:696-706 (1992).
Phuangsab, et al., *Cancer Lett*, 172:27-36 (2001).
Pichelmair, et al., *Science*, 314:997-1001 (2006).
Plumet, et al., *PLoS ONE*, 3(e279):1-10 (2007).
Poeck, et al., *Blood*, 103(8):3058-3064 (Apr. 2004) (www.bloodjournal.org/cgi/content/full/103/8/3058#REF4).
Poeck, et al., *Nature Medicine*, 14(11):1256-1262 (2008).
Portela, et al., *J. Gen. Virol.*, 2992(83):723-734 (2002).
Radecke, et al., *Embo J*, 14:5773-84 (Dec. 1, 1995).
Ranjith-Kumar, et al., *J. Virol.*, 76(24):12526-12536 (2002).
Ranjith-Kumar, et al., *RNA*, 12:303-312 (2006).

(56) References Cited

OTHER PUBLICATIONS

Reynolds, et al., *Nat Biotechnol*, 22:326-30 (2004).
Roempp, Sequenzhomologie, Georg Thieme Verlag KG, https://roempp.thieme.de/roempp4.0/do/data/RD-19.01964.
Rohayem, et al., *Journal of Virology*, 80(14):7060-7069 (2006).
Rosa, et al., *Molecular and Cellular Biology*, 1(9):785-796 (Sep. 1981).
Rossi, *Gene Therapy* 13:583-584 (2006).
Rothenfusser, et al., *J•Immunol*, 175:5260-8 (Oct. 15, 2005).
Rozenski, et al., *Nucleic acids research*, 27:196-97 (Jan. 1, 1999).
Rubin, et al, *Lancet*, 369:1731-41 (2007).
Rudd, et al., *J Immunol*, 176:1937-42 (Feb. 1, 2006).
Russell, *Cancer Gene Ther*, 9:961-966 (2002).
Samanta, et al., *The EMBO Journal*, 25:4207-4214 (Aug. 2006).
Schlee, et al., *Immunity*, 31:25-34 (2009).
Schlee, et al., *CTMI*, 316:207-230 (2007).
Schlee, et al., *Mol Ther*, 18(7):1254-1262 (2010).
Schlee, et al., *Molecular Therapy*, 14(4):463-470 (2006).
Schmidt, et al., *PNAS*, 106(29):12067-12072 (2009).
Schnell, et al., *EMBO J*, 13(18):4195-4203 (1994).
Schoatzau, et al., *Chem. Commun.*, 3:387-388 (1996).
Selisko, et al., *Virology*, 351(1):145-158 (2006).
Seth, et al., *Cell*, 122(5):669-82 (Sep. 9, 2005).
Shatkin, et al., *Nat Struct Biol*, 7(10):838-42 (Oct. 2000).
Singh, et al., *PNAS USA*, 86:8280-3 (Nov. 1989).
Sioud, *Advanced Drug Delivery Reviews*, 59(2-3):153-163 (2007).
Sioud, et al., *Biochem Biophys Res Commun*, 312(4):1220-1225 (2003).
Sioud, et al., *J Mol Biol*, 348:1079-1090 (2005).
Sioud, *Eur J Immunol*, 36(5):1222-30 (2006).
Soutschek, et al., *Nature*, 432(7014):173-178 (Nov. 2004).
Sproat, et al., *Nucleic acids research*, 27(8):1950-1955 (1999).
Stetson, et al., *J.Exp.Med.* 203:1837-41 (2006).
Stojdl, et al., *Nat Med*, 6:821-825 (2000).
Strahle, et al., *Virology*, 351(1):101-11 (2006).
Stump, et al., *Nucleic Acids Research*, 21(23):5480-5484 (1993).
Sugiyama, et al., *J Immunol*, 174:2273-2279 (2005).
Sumpter, Jr., et al., *J Virol* 79, 2689 (Mar. 2005).
Tabeta, et al., *Proc Natl Acad Sci USA*, 101:3516-21 (Mar. 9, 2004).
Takahasi, et al., *Molecular Cell*, 29:428-440 (Feb. 29, 2008).
Tormo, et al., *Am J Pathol*, 169:665-72 (2006).
Tormo, et al., *Cancer Res.*, 66:5427-35 (2006).
Tschoep, et al., *J Mol Med*, 79:306-13 (2001).
Tschopp, et al., *Nature Reviews*, 4:95-104 (Feb. 2003).
Uno, et al., *Nat. Med.*, 12:693-8 (2006).
Urban-Klein, et al., *Gene Therapy*, 12(5):461-466 (2005).
Van Dijk, et al., *J. Gen. Virol.*, 85:1077-1093 (2004).
Van Dijk, et al., *Virology*, 211:320-323 (1995).
Van Holten, et al., *Arthritis Research*, 4:346-352 (2002).
Vollmer, et al., *Antisense Nucleic Acid Drug Dev*, 12:165-75 (Jun. 2002).
Wagner, et al., ROEMPP Online, Version 3.36, catchword "Lipofektion" (= engl. "lipofection").
Walther, et al., *Drugs*, 60(2):249-271 (Aug. 2000).
Wang, et al., *J Med Chem.* 47:6902-6913 (2004).
Wang, et al., *Nat Struct & Mol Biol*, 17(7):781-787 (Jul. 2010).
Weber, et al., *J Virol*, 80(10):5059-64 (May, 2006).
Whelan, et al., *Curr. Topics in Microbiol. and Immunol.*, 283:61-119 (2004).
Wu, et al., *Brain Research*, 1008(2):284-287 (May 22, 2004).
Xiao, et al., *Annual review of biochemistry*, 71:165-89 (2002).
Xu, et al., *Mol Cell.* 19(6):727-40 (Sep. 16, 2005).
Yang, et al., *Embo J*, 14(24):6095-6106 (Dec. 15, 1995).
Yang, et al., *Immunity*, 23(5):465-78 (Nov. 2005).
Yoneyama, et al., *Nat. Immunol.*, 5(7):730-737 (Jul. 2004).
Yoneyama, et al., *J. Biol.Chem.*, 282:15315-8 (2007).
Yoneyama, et al., *Journal of Immunlogy*, 175:2851-2858 (2005).
Yount, et al., *Archives of Biochemistry and Biophysics*, 113:288-295 (1966).
Zeh, et al., *Cancer Gene Ther*, 9:1001-1012 (2002).
Zimmermann, et al., *Nature*, 441(7089):111-114 (May 2006).
Zlatev, et al., *Org Lett*, 12(10):2190-2193 (2010).
EP 1 920 775—Complete File Wrapper.

\* cited by examiner

Scheme 1 pppRNA 21 mer pppRNA 24 mer gamma modification

Q=alkyl R>12, aminoacids , peptids ,aminoacid analogs , lipids , phospholipids extended chain

PURIFICATION OF TRIPHOSPHORYLATED OLIGONUCLEOTIDES USING CAPTURE TAGS

CROSS REFERENCE TO RELATED APPLICATION

This application is a 35 U.S.C. 371 National Phase Entry Application from PCT/EP2012/055520, filed Mar. 28, 2012, which claims the benefit of Europe Patent Application No. 11160032.6 filed on Mar. 28, 2011, the disclosure of which is incorporated herein in its entirety by reference.

The present invention relates to a method of preparing triphosphate-modified oligonucleotides using a capture tag. The method allows the synthesis and purification of triphosphate-modified oligonucleotides in high yield and purity suitable for pharmaceutical applications.

BACKGROUND OF THE INVENTION

Schlee et al., *Immunity*, 2009, 31, 25-34 describe blunt-ended double stranded RNAs carrying a 5'-O-triphosphate moiety on one of the strands that act as potent stimulators of the immune system by binding the RIG-I helicase. Thus, there is a need to provide a simple and efficient method for preparing triphosphate-modified oligonucleotides in high purity, suitable for pharmaceutical applications.

The coupling of triphosphate groups or analogues thereof to the 5'-OH group of nucleosidic compounds is well known in the art. Ludwig J. et al., *J. Org. Chem.*, 1989, 54, 631-635 disclose a solution triphosphorylation method for preparing 5'-O-triphosphates of nucleosides and analogues using 2-chloro-4H-1,3,2-benzodioxaphosphorin-4-one as the phosphitylating agent. Gaur R. K. et al., 1992, *Tetrahedron Letters*, 33, 3301-3304 describe the use of said method on solid-phase for the synthesis of 2'-O-methylribonucleoside 5'-O-triphosphates and their $P_\alpha$-thio analogues. U.S. Pat. No. 6,900,308 B2 discloses the solid-phase synthesis of modified nucleoside 5'-β-triphosphates as potential antiviral compounds and U.S. Pat. Nos. 7,285,658, 7,598,230 and 7,807,653 disclose triphosphate analogues of nucleosides with modifications in the sugar, nucleobase and in the triphosphate entity. WO96/40159 describes a method for producing capped RNA or RNA analogue molecules, wherein an RNA or RNA analogue oligonucleotide is reacted with a phosphitylating agent such as 2-chloro-4H-1,3,2-benzodioxaphosphorin-4-one or a ring-substituted derivative thereof. The resulting intermediate is reacted with a phosphate or pyrophosphate or salt thereof, oxidized or hydrolyzed. The di- or triphosphorylated RNA or RNA analogue is capped by reacting with an activated $m^7G$ tri-, di- or monophosphate or analogue.

WO 2009/060281 describes immune stimulatory oligoribonucleotide analogues containing modified oligophosphate moieties and methods for the preparation of such compounds. This method includes the synthesis of the oligonucleotide on a solid support, reacting a nucleotide at a 5'-end of the oligonucleotide with a phosphitylating agent such as 2-chloro-4H-1,3,2-benzodioxaphosphorin-4-one in a suitable solvent and in the presence of a base, reacting the phosphitylated oligonucleotide with a pyrophosphate or pyrophosphate analogue, oxidizing the oligonucleotide with an oxidizing agent and deprotecting the oligonucleotide to give a triphosphate- or triphosphate analogue-modified oligonucleotide.

Polyacrylamide gel-electrophoresis as employed in WO 96/40159 is applicable only for small scale separations. The resolution power of ion exchange chromatography for 5'-mono-, di-, triphosphorylated products of longer oligoribonucleotides is limited. The required denaturing conditions make separation a tedious task (Sproat, 1999; Zlatev, 2010; WO 2009/060281), moreover, products are usually contaminated with n–1, n–2 sequences and their mono- and diphosphates resulting in insufficient purity. Given the sensitivity for precise terminal structures of the RIG-I ligands, these purification methods are suboptimal for pharmacological applications.

Dual targeting strategies (siRNA and RIG ligand) require general sequence independent purification methods.

SUMMARY OF THE INVENTION

It is highly desirable to produce 5'-O-triphosphorylated oligonucleotides and their analogues in large scale for potential clinical use, and a convenient preparation method would be highly desirable. In the present application it is shown that the 5'-O-cyclotriphosphate intermediate of a solid-phase bound fully protected oligonucleotide (see FIG. 1) can be ring opened with a capture tag, e.g. decylamine to give a linear $P_\gamma$ tagged species that is stable to the deprotection of the RNA. The nature of the tag is such as to impart a specific retention of the capture tagged triphosphate species on a capture tag specific reagent, enabling easy separation from the impurities that do not contain the tag. The tag can be subsequently removed if desired. The method can be extended to encompass analogues of the triphosphate moietity, e.g. analogues containing for instance β,γ-methylene, fluoromethylene, difluoromethylene and imino groups replacing an oxygen atom.

Advantages of the capture tagging method are simple purification and improved recovery of the desired species, e.g. at room temperature by RP-HPLC or affinity chromatography, optionally followed by cleavage of the capture tag under suitable conditions.

DETAILED DESCRIPTION OF THE PREFERRED EMBODIMENTS

The present invention describes the synthesis and purification of oligonucleotide triphosphates, including analogues thereof that contain capture tags. The most widely employed method for the HPLC purification of standard 5'-OH oligonucleotides is reversed phase chromatography of trityl-ON oligonucleotides.

The method described in this invention offers a practical solution with similar efficacy for 5'-triphosphorylated oligonucleotides.

Thus, a subject-matter of the present invention is a method of preparing an oligonucleotide of formula (I),

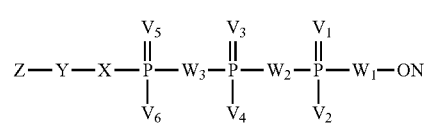

wherein $V_1$, $V_3$ and $V_5$ are independently in each case selected from O, S and Se;

$V_2$, $V_4$ and $V_6$ are independently in each case selected from OH, $OR^1$, SH, $SR^1$, F, $NH_2$, $NHR^1$, $N(R^1)_2$ and $BH_3^- M^+$, $W_1$ is O or S, $W_2$ is O, S, NH or $NR^2$, $W_3$ is O, S, NH, $NR^2$, $CH_2$, CHHal or $C(Hal)_2$, $R^1$, $R^2$ and $R^3$ are selected from $C_{1-6}$ alkyl, $C_{2-6}$ alkenyl, $C_{2-6}$ alkynyl, $C_{2-6}$ acyl or a cyclic group, each optionally substituted, or wherein two $R^1$ may form a ring together with an N-atom bound thereto, $M^+$ is a cation, X is NH, $NR^3$, O or S, Z represents a capture tag, Y represents a bond or a linker connecting the capture tag to X, and ON represents an oligonucleotide comprising at least 4 nucleotide or nucleotide analogue building blocks, comprising the steps:

(a) reacting a compound of formula (IIa)

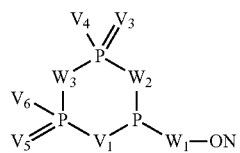

(IIa)

wherein $V_1$, $V_3$, $V_5$, $V_4$, $V_6$, $W_1$, $W_2$, $W_3$, and ON are as defined above, with an oxidizing agent to obtain a compound of formula (IIb)

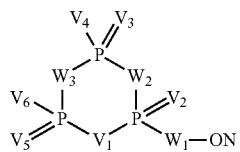

(IIb)

wherein $V_1$, $V_3$, $V_5$, $V_2$, $V_4$, $V_6$, $W_1$, $W_2$, $W_3$ and ON are as defined above, (b) reacting the oxidized compound with a capture tag agent of formula (III),

Z—Y—XH    (III)

wherein X, Z, and Y are as described above to obtain a reaction product comprising the oligonucleotide of formula (I), and (c) contacting the reaction product of step (b) with a reagent capable of interacting with the capture tag under conditions which allow separation of the oligonucleotide (I) from other species contained in said reaction product.

Optionally, the method further comprises the step (d) removing the capture tag to obtain an oligonucleotide of formula (IV),

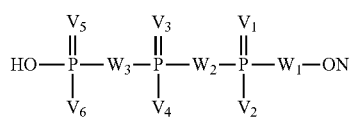

(IV)

wherein $V_1$, $V_3$, $V_5$, $V_2$, $V_4$, $V_6$, $W_1$, $W_2$, $W_3$ and ON are as described above. This step is carried out under conditions which do not cause degradation of the triphosphate moiety, e.g. as described in detail below.

In further embodiments, the capture tag is not or not completely removed. In these embodiments, the tagged oligonucleotide as such may have utility, e.g. utility as pharmaceutical agent.

The term "oligonucleotide" in the context of the present application encompasses compounds comprising a plurality, e.g. at least 4 nucleotide or nucleotide analogue building blocks. Preferably, the oligonucleotide comprises 6-100, e.g. 20-40 building blocks. The nucleotide or nucleotide analogue building blocks may comprise nucleoside or nucleoside analogue subunits connected by inter-subunit linkages. The nucleoside subunits include deoxyribonucleoside subunits, ribonucleoside subunits and/or analogues thereof, particularly sugar- and/or nucleobase-modified nucleoside analogues. Further, the oligonucleotides may comprise non-nucleotidic building blocks and/or further terminal and/or side-chain modifications.

In preferred sugar-modified subunits the 2'-OH of a ribonucleoside subunit is replaced by a group selected from OR, R, halo, SH, SR, $NH_2$, NHR, $NR_2$ or CN, wherein R is $C_{1-6}$ alkyl, $C_{2-6}$ alkenyl or $C_{2-6}$ alkynyl and halo is F, Cl, Br or I. In further preferred sugar-modified subunits, the ribose may be substituted, e.g. by another sugar, for example a pentose such as arabinose. This sugar modification may be combined with 2'-OH modifications as described above, such as in 2'-fluoro-arabinonucleoside subunits. Still further preferred sugar-modified subunits include locked nucleosides (LNA) or 2',3'-seco-nucleosides (UNA). In preferred nucleobase-modified nucleosidic building blocks, a non-standard, e.g. non-naturally occurring nucleobase, is used instead of a standard nucleobase. Examples of non-standard nucleobases are uracils or cytosines modified at the 5-position, e.g. 5-(2-amino)propyl uracil or 5-bromouracil; hypoxanthine; 2,6-diaminopurine; adenines or guanines modified at the 8-position, e.g. 8-bromoguanine; deazanucleosides, e.g. 7-deazaguanine or 7-deazaadenine; or O- and N-alkylated nucleobases, e.g. $N^6$-methyladenine, or $N^6,N^6$-dimethyladenine. Further suitable nucleobase analogues may be selected from universal nucleobase analogues such as 5-nitroindole.

The inter-subunit linkage between subunits may be a phosphodiester linkage or a modified linkage, e.g. a phosphorothioate, phosphorodithioate, methylphosphonate, phosphoramidate, boranophosphate, or another modified linkage known to a skilled person in the art.

The oligonucleotide may be selected from deoxyribonucleotides, ribonucleotides and oligonucleotide analogues. Analogues of desoxyribonucleotides or ribonucleotides may comprise at least one desoxyribonucleoside or ribonucleoside subunit and at least one modified nucleosidic subunit and/or at least one modified inter-subunit linkage, e.g. as described above. Oligonucleotide analogues may also consist in their entirety of modified nucleosidic subunits.

The oligonucleotide may be a single-stranded molecule or a double-stranded molecule. Double-stranded oligonucleotides may comprise completely or partially complementary strands. Double-stranded molecules may be blunt-ended or comprise at least one overhang, e.g. a 5'- or 3'-overhang. Overhangs, if present, are preferably located at the distal end of the molecule (with regard to the triphosphate/triphosphate analogue group). Double-stranded oligonucleotides may also comprise a hairpin-structure, wherein the duplex is closed by a loop at the distal end thereof (with regard to the triphosphate/triphosphate analogue group). The loop may comprise nucleotide and/or non-nucleotide building blocks, for example diol-based building blocks such as ethylene glycol moieties, e.g. tri(ethylene)glycol or hexa(ethylene)glycol; propane-1,3-diol, dodecane-1,12-diol; or 3,12-dioxa-7,8-dithiatetradecane-1,14-diol.

In a preferred embodiment, double-stranded molecules are blunt-ended, particularly at the proximal end thereof (with regard to the triphosphate/triphosphate analogue group).

The oligonucleotide may comprise further terminal and/or side-chain modifications, e.g. cell specific targeting entities covalently attached thereto. Those entities may promote cellular or cell-specific uptake and include, for example lipids, vitamins, hormones, peptides, oligosaccharides and analogues thereof. Targeting entities may e.g. be attached to modified nucleobases or non-nucleotidic building blocks by methods known to the skilled person.

The oligonucleotide of formula (I) or (IV) comprises a triphosphate/triphosphate analogue group. In this group, $V_1$, $V_3$ and $V_5$ are independently selected from O, S and Se. Preferably, $V_1$, $V_3$ and $V_5$ are O. $V_2$, $V_4$ and $V_6$ are in each case independently selected from OH, $OR^1$, SH, $SR^1$, F, $NH_2$, $NHR^1$, $N(R^1)_2$ and $BH_3^-M^+$. Preferably, $V_2$, $V_4$ and $V_6$ are OH. $R^1$ may be $C_{1-6}$ alkyl, $C_{2-6}$ alkenyl, $C_{2-6}$ alkynyl, $C_{2-6}$ acyl or a cyclic group, e.g. a $C_{3-8}$ cyclo(hetero)alkyl group, a $C_{3-6}$ cyclo(hetero)alkenyl group, phenyl or $C_{5-6}$ heteroaryl group, wherein heteroatoms are selected from N, O and S. Further, two $R^1$ may form a ring, e.g. a 5- or 6-membered ring together with an N-atom bound thereto. $R^1$ may also comprise substituents such as halo, e.g. F, Cl, Br or I, O(halo)$C_{1-2}$ alkyl and—in the case of cyclic groups—(halo)$C_{1-2}$ alkyl. $M^+$ may be an inorganic or organic cation, e.g. an alkali metal cation or an ammonium or amine cation.

$W_1$ may be O or S. Preferably, $W_1$ is O. $W_2$ may be O, S, NH or $NR^2$. Preferably, $W_2$ is O. $W_3$ may be O, S, NH, $NR^2$, $CH_2$, CHHal or C(Hal)$_2$. Preferably, $W_3$ is O, $CH_2$ or $CF_2$. $R^2$ may be selected from groups as described for $R^1$ above. Hal may be F, Cl, Br or I.

The triphosphate/triphosphate analogue group is preferably attached to a terminus of the oligonucleotide. Preferably, the group is attached to the 5'-terminus of the oligonucleotide, particularly to the 5'-OH-group of the 5'-terminal sugar thereof.

Step (a) of the method of the invention comprises the reaction of cyclic P(V)—P(V)—P(III) species of formula (IIa) with an oxidizing agent. The compound of formula (IIa) may be obtained according to standard methods as described by Ludwig et al, 1989, supra and Gaur et al., 1992, supra, namely by reacting the 5'-terminal OH-group of an oligonucleotide with a trifunctional phosphitylating agent, e.g. 2-chloro-4H-1,3,2-benzodioxaphosphorin-4-one under suitable conditions, e.g. in the presence of base (pyridine or diisopropylmethylamine) in a suitable solvent such as dioxane or dichloromethane, and subsequent reaction with pyrophosphate ($W_3$=O) or a modified pyrophosphate ($W_3$ is different from O, e.g. $CH_2$, $CCl_2$, NH or $CF_2$). Preferably, a tri-n-butylammonium salt of the pyrophosphate or modified pyrophosphate in DMF is used. The resulting cyclic P(III)—P(V) intermediate (IIa) is then oxidized under anhydrous conditions, e.g. with a peroxide, such as t-butyl hydroperoxide, cumene hydroperoxide, (10-camphorsulfonyl)oxaziridine. Alternatively, phenylacetyldisulfide ($V_2$=S), or borane-diisopropylethylamine complex ($V_2$=$BH_3$) can also be employed respectively, to give the corresponding cyclic 5'-triphosphate/triphosphate analogue of formula (IIb). Reference in this context is also made to WO 96/40159 or WO 2009/060281, the contents of which are herein incorporated by reference.

Reaction step (a) may take place with an oligonucleotide in solution or with an oligonucleotide bound to a solid phase, e.g. an organic resin or glass, such as CPG. The oligonucleotide may further comprise protecting groups, e.g. sugar- or nucleobase protecting groups that are well known to the skilled person. Preferred examples of protecting groups are 2-cyanoethyl for the internucleoside phosphodiester or phosphorothioate, tert-butyldimethylsilyl, triisopropylsilyloxymethyl or bis(acetoxyethoxy)methyl for the ribose 2'-hydroxyl group, 4-t-butylphenoxyacetyl or phenoxyacetyl, acetyl, isobutyryl, benzoyl for the exocyclic amino groups of the nucleobases. More preferably, step (a) is carried out with a solid-phase bound oligonucleotide.

According to step (b) of the method of the invention, compound (IIb) is reacted with a capture tag agent of formula (III)

Z—Y—XH       (III)

wherein X is a group selected from NH, $NR^3$, O or S. $R^3$ is defined as described above for $R^1$. Preferably, X is NH or S.

The capture tag is functionally defined below by a series of plausible Examples. A general rule may be Z has to allow a convenient purification, and it should be removable under conditions which are compatible with pppRNA stability requirements.

Y represents a chemical bond or a linker, e.g. an alkylene, preferably a $C_{1-6}$-alkylene linker, more preferably a $C_{2-5}$-alkylene linker, or aralkylene linker, optionally comprising heteroatoms or heteroatom-containing groups, such as O, S, NH, C=O or C=S, and/or optionally comprising C=C or C≡C bonds.

In another preferred embodiment the linker is a polyalkylene oxide, preferably a poly-$C_2$-$C_6$-alkylene oxide, more preferably a poly-$C_2$-$C_3$-alkylene oxide. The number average molecular weight of the linker may be in the range from 30-800 g/mol, preferably from 40-450 g/mol, more preferably from 40-250 g/mol. The linker may be [—$CH_2CHR^4$—O—]$_n$ with n=1-10, preferably n=1-7, more preferably n=2-5, and even more preferably n=3. $R^4$ may be H or $C_{1-6}$-alkyl.

In a preferred embodiment $R^4$ is H.

In an especially preferred embodiment the linker has the formula —$CH_2$—$CH_2$—[(O—$CH_2CH_2$)]$_3$—.

Reaction step (b) may take place with an oligonucleotide in solution or with an oligonucleotide bound to a solid phase, e.g. an organic resin or glass. The oligonucleotide may further comprise protecting groups as described above. More preferably, step (b) is carried out with a solid phase-bound oligonucleotide.

The capture tag Z according to the present invention is a moiety capable of non-covalently or covalently interacting with a capture reagent under conditions which allow separation for compounds comprising the capture tag, e.g. the oligonucleotide (I) from other species, which do not contain the capture tag. Preferably, the capture reagent is an immobilized reagent or a reagent capable of being immobilized.

Suitable capture tags are for instance long-chain, e.g. $C_{8-24}$, preferably $C_{13-24}$ aliphatic alkyl residues such as decyl or octadecyl or other lipidic/lipophilic residues such as e.g. cholesteryl or tocopheryl. In this case, the tagged triphosphate entity can be captured and purified on a solid phase by standard reversed phase chromatography, e.g. RP-HPLC, or by hydrophobic interaction chromatography (HIC). The capture tag may also be a perfluoroalkyl entity, e.g. a 4-(1H,1H,2H,2H-perfluorodecyl)benzyl or a 3-(perfluorooctyl)propyl residue for specific capture of the modified oligo-triphosphate on a Fluorous Affinity support such as is commercially available from Fluorous Technologies, Inc.

In another embodiment, the capture tag may be a first partner of a non-covalent high-affinity binding pair, such as biotin, or a biotin analogue such as desthiobiotin, a hapten or an antigen, which has a high affinity (e.g. binding constant of $10^{-6}$ I/mol or less) with the capture reagent, which is a second complementary partner of the high-affinity binding pair, e.g. a streptavidin, an avidin or an antibody.

In yet another embodiment, the capture tag may be a first partner of a covalent binding pair, which may form a covalent bond with the capture reagent, which is a second complementary partner of the covalent binding pair, wherein the covalent bond may be a reversible or an irreversible bond. In this embodiment, the capture tag component Z may be a reactive chemical entity such as an azide or alkynyl group enabling covalent reaction with a capture reagent that contains a complementary reactive group, e.g. an alkynyl or azido moiety, respectively, in the case of the Husigen 3+2 cycloaddition reaction (the so-called "click-reaction" that is Cu(I) catalyzed or a variant thereof that proceeds without Cu(I) ions via release of severe ring strain in e.g. cyclooctyne derivatives). A specific example for Z—Y—X in such a case would be propargylamino.

In another embodiment, the capture tag component may be a chemical entity which contains an additional nucleophilic group, for instance a second amino group in an $NH_2$—Y—XH type reagent. A wide range of suitable electrophilic Z reagent such as cholesterol, chloroformiate or biotin N-hydroxy succinimide active esters may then be used to introduce the tagging group while the oligonucleotide is attached to the solid phase, thus significantly extending the scope of the tagging reaction.

In a preferred embodiment the capture tag is a long-chain alkyl residue, a perfluoroalkyl entity, an azide or an alkynyl group.

Moreover, Y may optionally contain a disulfide bond to enable recovery of the modified triphosphorylated oligonucleotide with a free sulfhydryl moiety connected via part of the linker through X to the γ-phosphorus.

In a further embodiment of the present invention, the oligonucleotide may carry a second capture tag at a different position, e.g. at the 3'-terminus. The first and the second capture tags are preferably selected as to allow purification by two orthogonal methods to enable recovery of extremely high purity material. For example the first capture tag may be a lipophilic group, which interacts with a suitable chromatographic support and the second capture tag may be biotin, which interacts with streptavidin.

The second capture tag may be conveniently introduced by performing the synthesis using a modified CPG (controlled glass support) for oligoribonucleotide synthesis.

Step (c) of the method of the present invention comprises contacting the reaction product of step (b), with a capture reagent capable of interacting with the capture tag Z under conditions which allow separation of the capture tag containing oligonucleotide (I) from other species contained in the reaction product. Before step (c), the solid phase bound oligonucleotide (I) is cleaved from the solid phase and deprotected, i.e. the protection groups are partially or completely removed. The capture reagent is preferably immobilized on a suitable support, e.g. a chromatographic support. In order to provide separation of capture tag containing oligonucleotide (I) from non-capture tag-containing species, the reaction products from step (b) are cleaved from a solid phase and deprotected, if necessary, and subjected to a separation procedure, preferably a chromatographic separation procedure based on the interaction of the capture tag Z with the capture reagent. During the separation step, the purity of the oligonucleotide (I), which is generally in the range of 25-70% for the crude material depending upon the length and complexity of the sequence, may be increased to 90%, 91%, 92%, 93%, 94%, 95% or more. For toxicity studies a purity of >85% is desirable, whereas in late stage clinical trials the purity should be in the range of at least 90-95%. Thus, the present invention provides a way to obtain a high purity pppRNA as would be required for human clinical trials.

In step (c), the capture tag and the capture reagent capable of interacting therewith are preferably selected from (i) a hydrophobic or fluorinated group and a chromatographic material with affinity for hydrophobic or fluorinated groups, e.g. a reversed phase material or a fluorous affinity support; (ii) a first partner of a non-covalent high-affinity binding pair and a second complementary partner of a non-covalent high-affinity binding pair, (iii) a first partner of a covalent binding pair and a second complementary partner of a covalent binding pair, where the first and second partner form covalent bonds.

After the purification step (c), capture tag Z may be cleaved from the triphosphate-modified oligonucleotide in a further step (d) resulting in an untagged oligonucleotide (IV).

Step (d) has to be compatible with stability requirements of the triphosphate end product and with stability requirements of the interribonucleotide bond. It may comprise cleavage by mildly acidic conditions when X is NH, cleavage with silver ions when X is S, cleavage by a thiol such as dithiothreitol leading to elimination of thiirane when Y—X—P contains —S—S—$CH_2$—$CH_2$—O—P.

In further embodiments, the capture tag set remains completely or partially on the triphosphate-modified oligonucleotide, particularly when the tagged oligonucleotide is suitable for pharmaceutical applications. In these embodiments, the reagent Z—Y—XH has to be selected from a subgroup of Z-residues, which are functionally compatible with the structural requirements of the RIG-I sensor. For instance, the Z=decyl-octadecyl, Y=link XH=NH combination is known to fulfill these requirements.

The triphosphate/triphosphate analogue modified oligonucleotides produced according to the present invention are particularly suitable for pharmaceutical applications due to their high purity. In an especially preferred embodiment, the oligonucleotide (I) or (IV) is an activator of RIG-1 helicase. Specific examples of suitable RIG-1 activators are disclosed in Schlee et al., 2009, supra, the content of which is herein incorporated by reference.

In another embodiment the present invention refers to oligonucleotides of Formula (I), obtainable by a method according to the present invention.

Still another subject-matter of the invention is the use of a kit for preparing an oligonucleotide of formula (I)

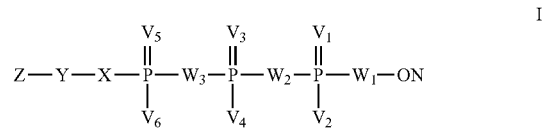

wherein $V_1$, $V_3$, $V_5$, $V_2$, $V_4$, $V_6$, $W_1$, $W_2$, $W_3$, X, Y, Z and ON are defined as above,
wherein the kit comprises (a) a capture tag agent of formula (III)

Z—Y—XH  (III)

wherein X, Z and Y are defined as above, and
(b) a capture reagent capable of interacting with the capture tag.

Still another subject-matter of the invention is a modified oligonucleotide of formula (I)

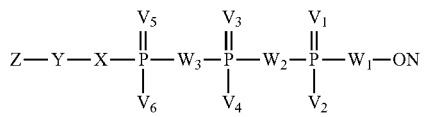

wherein

X is NH, O, R—O—[P(V$_1$)V$_2$—W$_1$]$_n$ or R—O—P(V$_3$)V$_4$—W$_2$—P—(V$_1$)V$_2$—W$_1$, n is 1-12, preferably 1 or 2, Y is a bond, Z is C$_{13}$-C$_{24}$ alkyl, Q or QNHC$_2$-C$_{24}$ alkyl, Q is selected from H, aminoacids, aminoacid analogues, C$_1$-C$_{24}$ alkyl, preferably C$_{12}$-C$_{24}$ alkyl, peptides and lipids, R is C$_1$-C$_{24}$ alkyl, C$_2$-C$_{24}$ alkenyl, C$_2$-C$_{24}$ alkynyl and lipids, R is C$_1$-C$_{24}$ alkyl, C$_2$-C$_{24}$ alkenyl, C$_2$-C$_{24}$ alkynyl, C$_2$-C$_{24}$ acyl or a cyclic group, and optionally substituted, and V$_1$, V$_2$, V$_3$, V$_4$, V$_5$, V$_6$, W$_1$, W$_2$, W$_3$ and ON are defined as in any one of claims 1-11, wherein V$_1$, V$_2$, V$_3$, V$_4$, V$_5$, V$_6$, W$_1$, W$_2$ and W$_3$ are preferably O.

According to a preferred embodiment of the present invention a modified oligonucleotide of formula (I) has X being NH. This embodiment preferably has Z being Q or Z being QNHC$_2$-C$_{24}$ alkyl, wherein in a particularly preferred embodiment C$_2$-C$_{24}$ alkyl is C$_2$ alkyl and/or Q is H. Particularly preferred embodiments of the identified oligonucleotide according to the invention are shown in FIG. 8.

Further, the present invention shall be explained in more detail by the following Figures and Examples.

FIG. 1 shows a schematic overview of the method of the invention using a decyl residue as capture tag Z FIG. 2 shows RP-HPLC purification of pppRNA via n-decyl-NH-pppRNA intermediate (A) crude reaction mixture containing 65% n-decyl-NH-pppRNA (peak at 14 min);

(B) isolated n-decyl-NH-pppRNA;

(C) pppRNA; the pH=3.8 60 min hydrolysis product from B

In FIG. 2 the x-axis means time [min] and the y-axis means absorbance at 260 nm [mAu].

The broad peak at 10 min retention time in A contains the nonphosphory-lated 24-mer, shorter synthesis failure sequences, the minor pppRNA hydrolysis product and the 5″-H-phosphonate derivative of the 24-mer. The insert shows the position of pppRNA and 5″-OH RNA in this system.

Column: Hamilton PRP-1 4.1×250 mm, 10 µm

Gradient: 1-100% B in 18 min, A=0.05 M TEAB; B=80% Methanol 0.05 M TEAB

FIG. 3 shows MALDI-TOF spectra α-axis: mass [Da]) corresponding to HPLC traces A, B and C in FIG. 2 respectively.

(A) spectrum recorded from the crude reaction mixture after desalting showing the presence of n-decyl-NH-ppp RNA (24d), pppRNA (24c), 5″-H-phosphonate RNA(24b) and 5″-OH—RNA(24a) and shorter synthesis failure sequences indicated as peaks 12-23;

(B) spectrum recorded from HPLC isolated n-decyl-NHpppRNA (B);

(C) spectrum of pure pppRNA as obtained from the direct EtOH precipitation of the pH=3.8 hydrolysis product of n-decyl-NH-pppRNA FIG. 4 shows a reaction scheme explaining the generation of side products 24 a-c FIG. 5 shows the time course for the conversion of n-decyl-NH-pppRNA to pppRNA via acidic hydrolysis of the phosphoramidate bond.

FIG. 6 shows typical MALDI spectra α-axis: mass [Da]) of 21-mer, 24-mer, 27-mer pppRNA products as obtained after capture tag removal and EtOH precipitation as Na$^+$ salt. The correct mass peak is observed at m/z 6911.6 (A), m/z 7828 (B), m/z 8808.1 (C) and the peaks at m/z 3462 (A), m/z 3918 (B), 4408 (C) are due to the doubly charged pppRNA, respectively. Similar quality spectra have been obtained in more than 50 examples with a variety of sequences containing nucleoside analogs and 3' modifications in the 15-42-mer range.

FIG. 7A shows a semipreparative scale reversed phase HPLC purification of a 1 µmol scale reaction of decyl-NHpppRNA 21 mer on a 7 mm Hamilton PRP-1 column Column: Hamilton PRP-1 7×250 mm, 10 µm Flow rate 3 mL/min.

Gradient: 1-80% B in 50 min, A=0.1M TEAB; B=80% Methanol 0.1 M TEAB

FIG. 7B and FIG. 7C show semipreparative scale reversed phase HPLC purifications, in particular showing how the inventive method is able to deal with sub-optimal synthesis and/or 5'-phosphorylation conditions.

In all figures the x-axis is volume [ml] and the y-axis is absorbance at 260 nm [mAu].

A. pppRNA, RT=9.3 min
B. n-decyl-NH-pppRNA, RT=13.8 min,
C. n-dodecyl-NH-pppRNA, RT=15.5 min
D. n-tetradecyl-NH-pppRNA, RT=17.3 min
E. n-octadecyl-NH-pppRNA, RT=19.7 min Example 1

Figure 1:
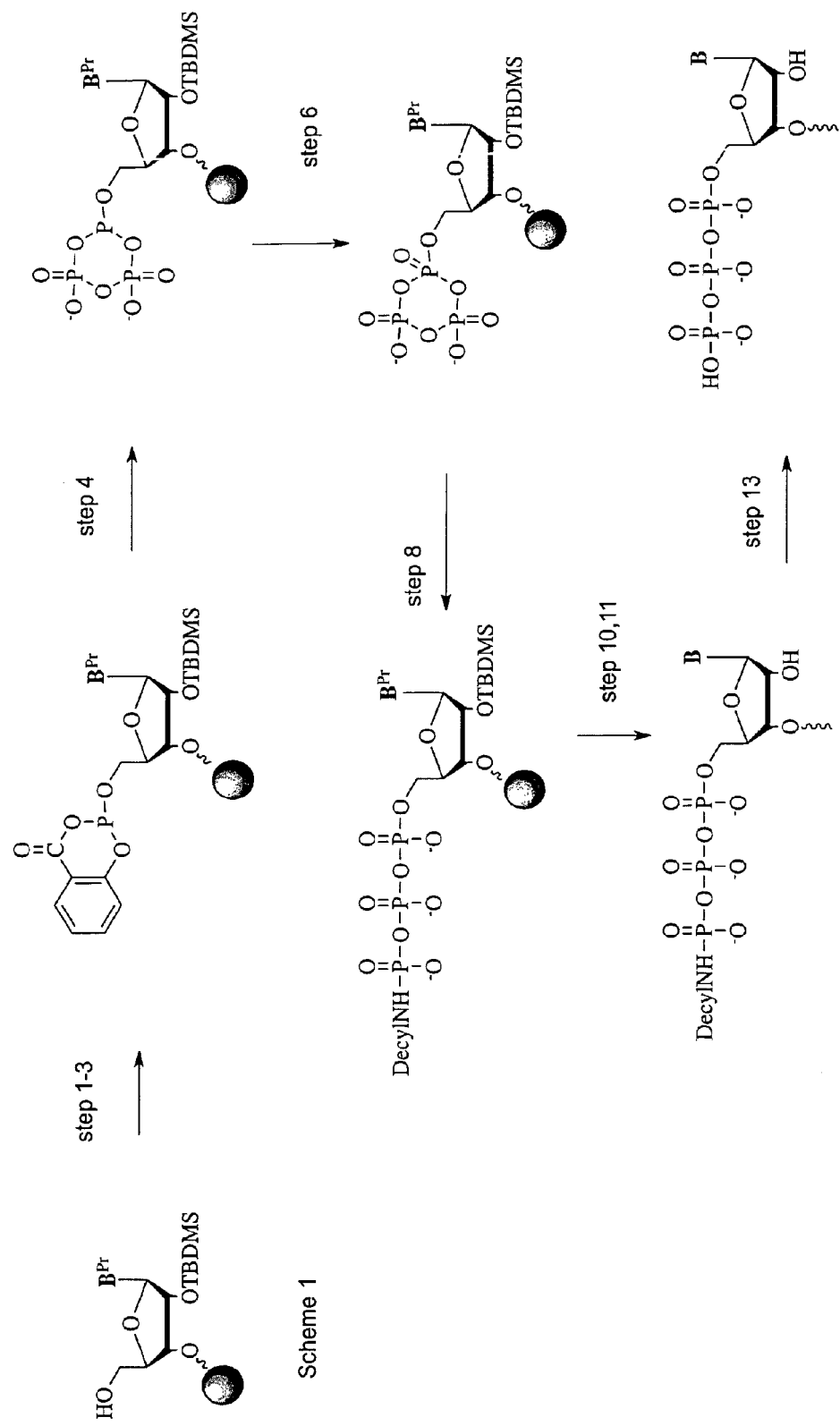
Figure 2A:
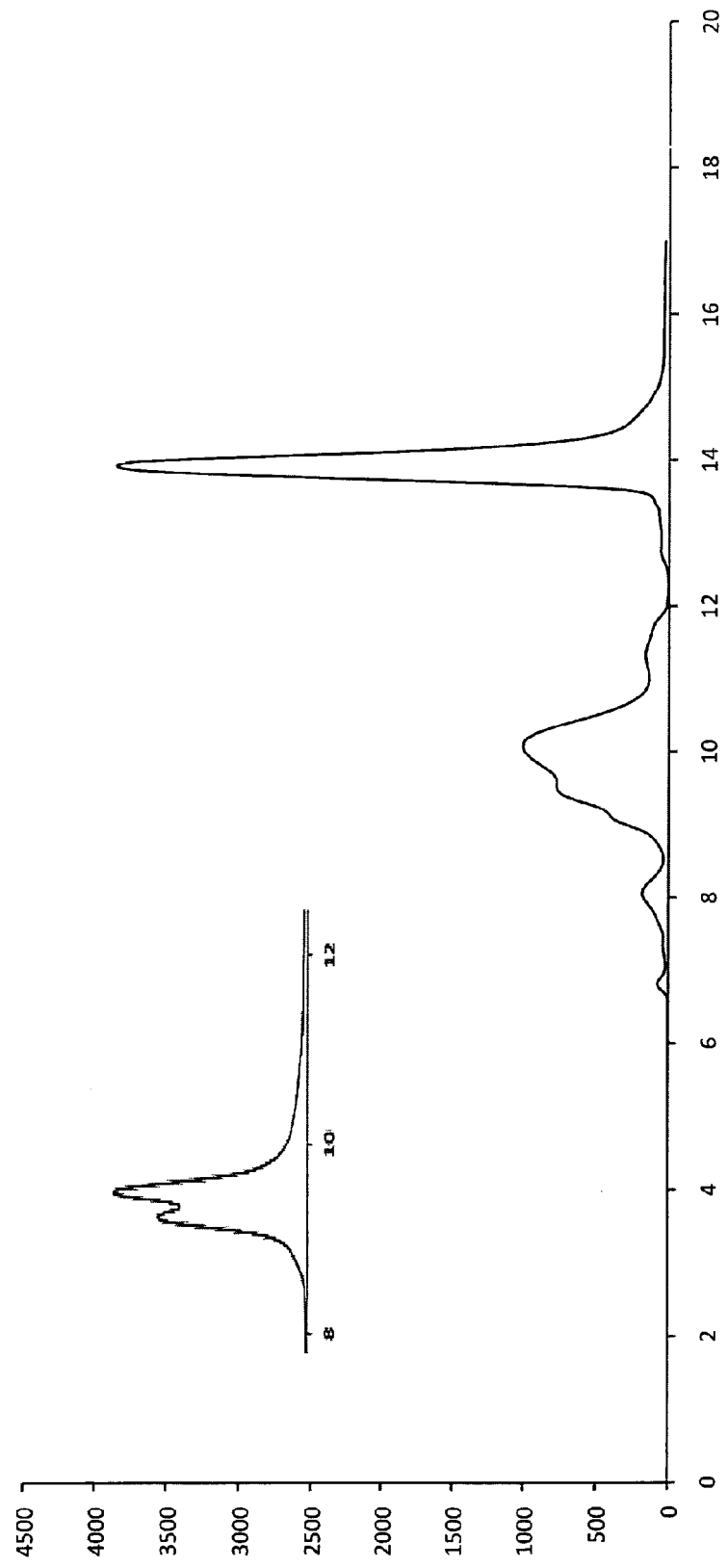
Figure 2B:
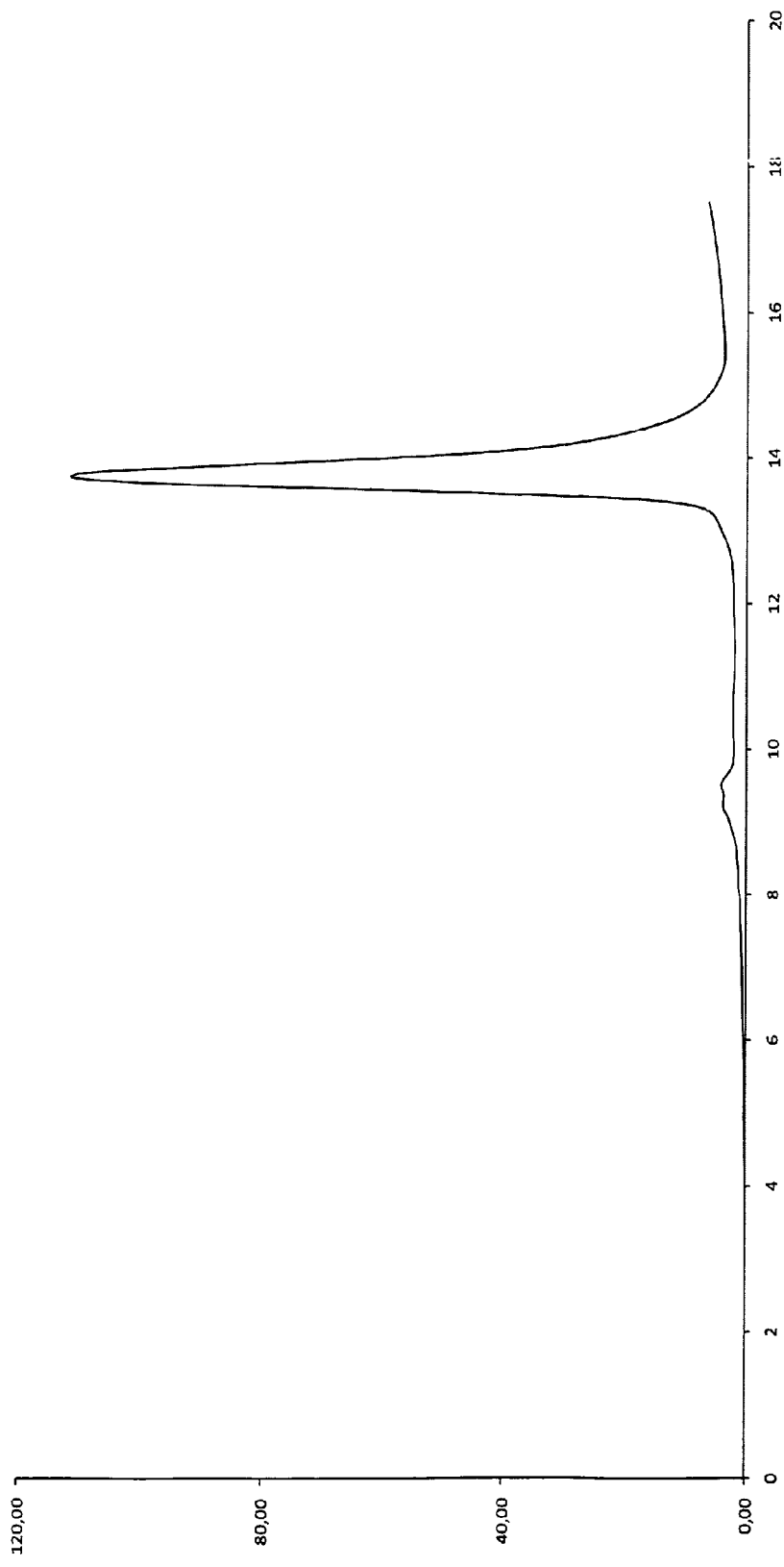
Figure 2C:
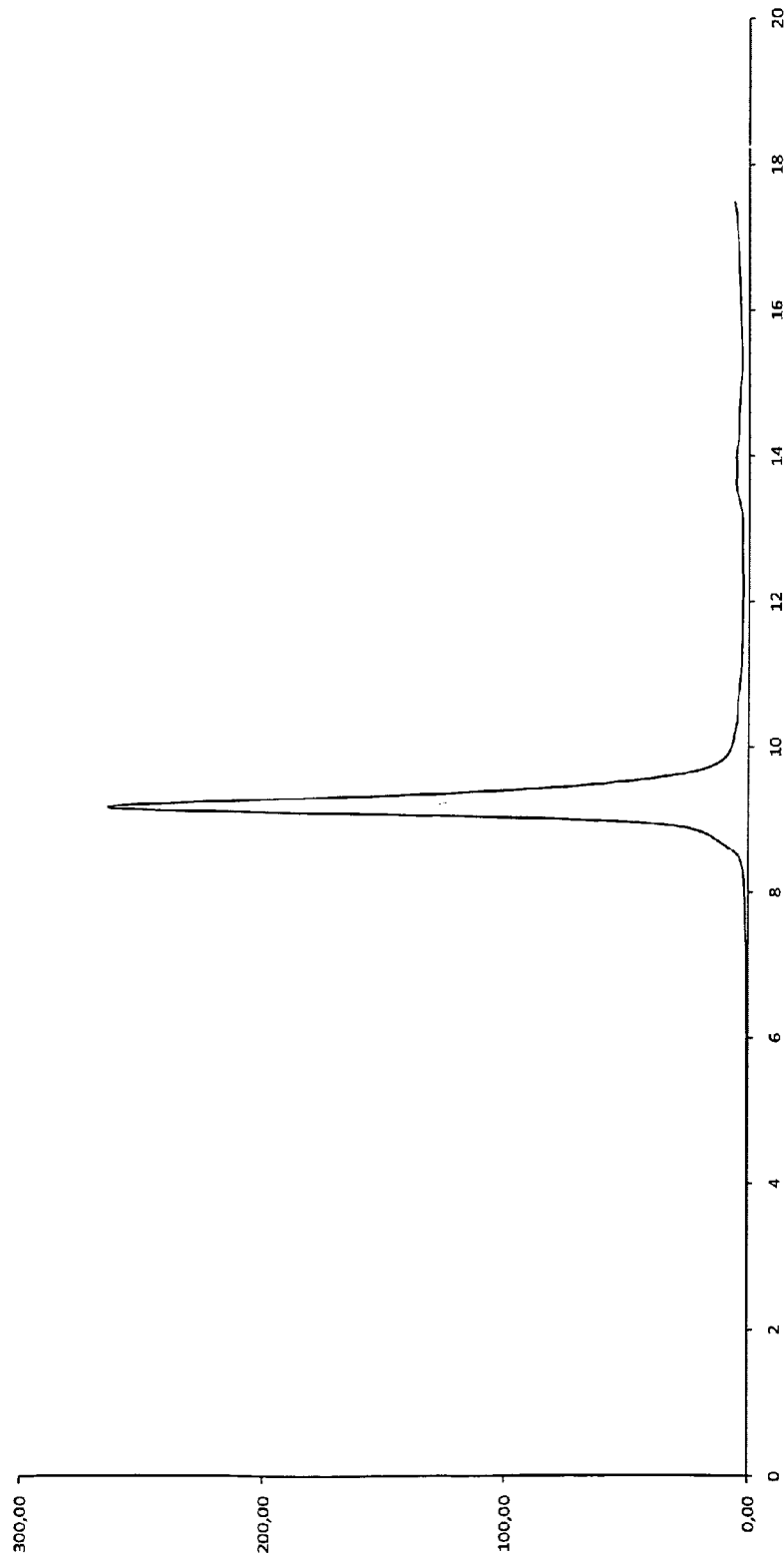
Figure 3A:
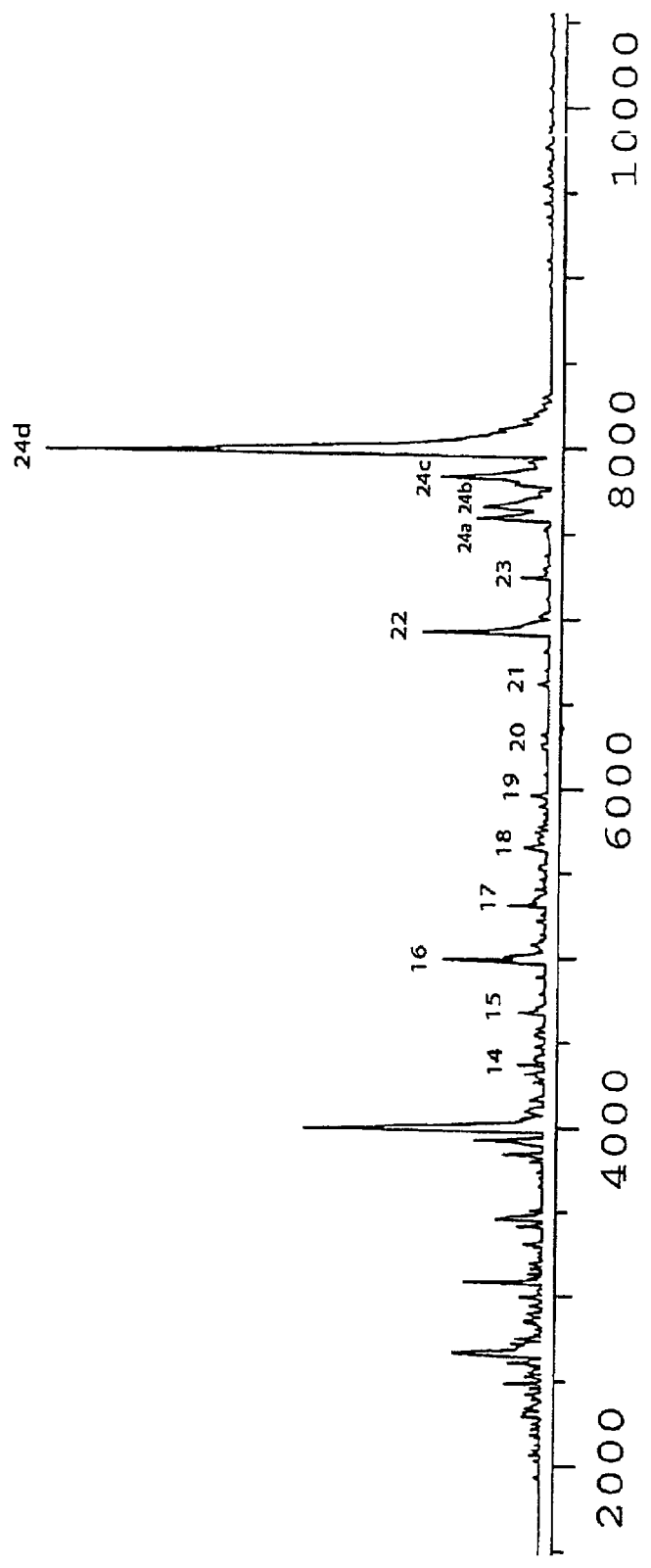
Figure 3B:
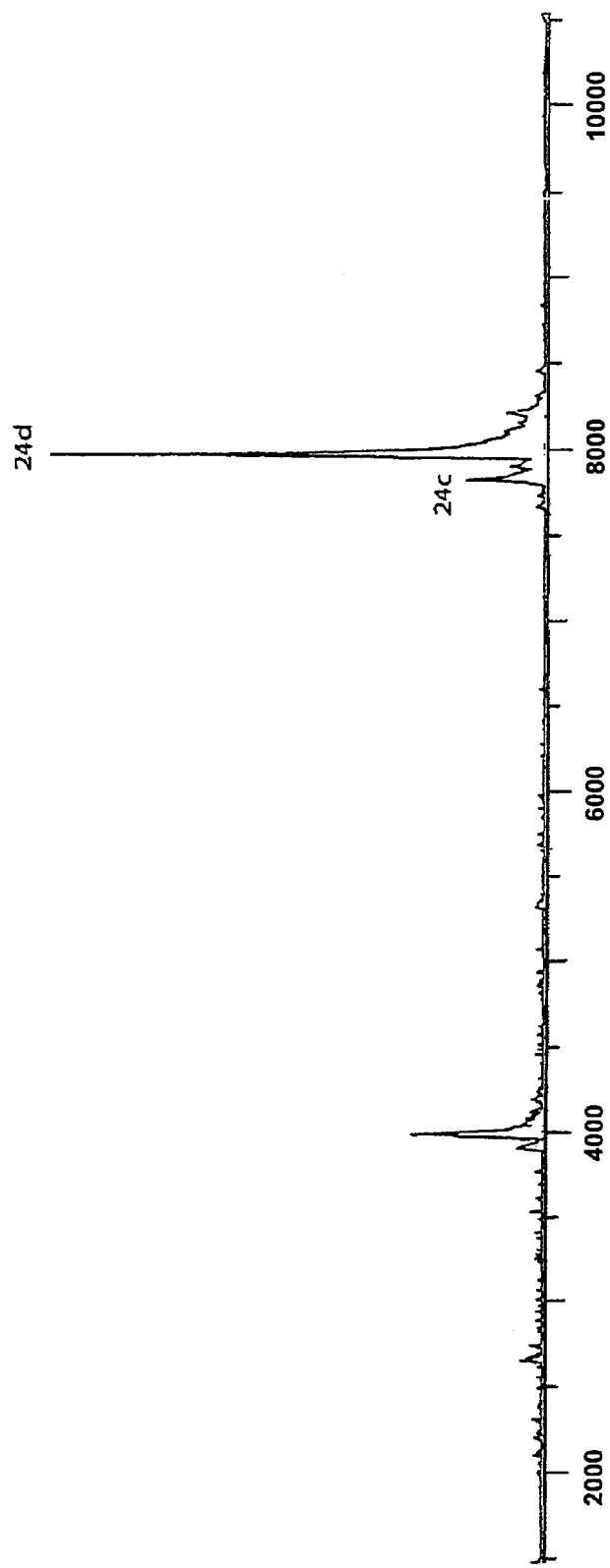
Figure 3C:
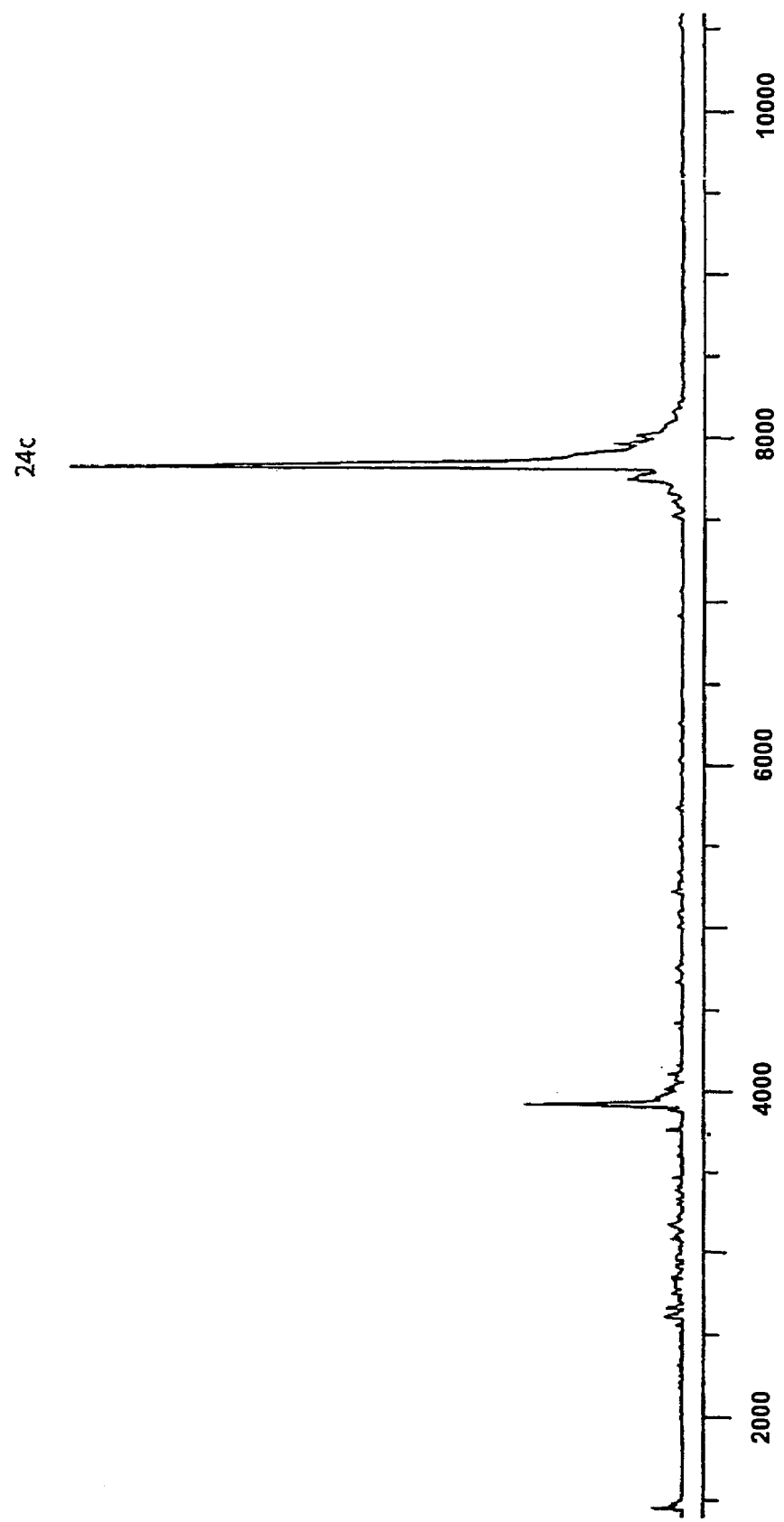
Figure 4A:
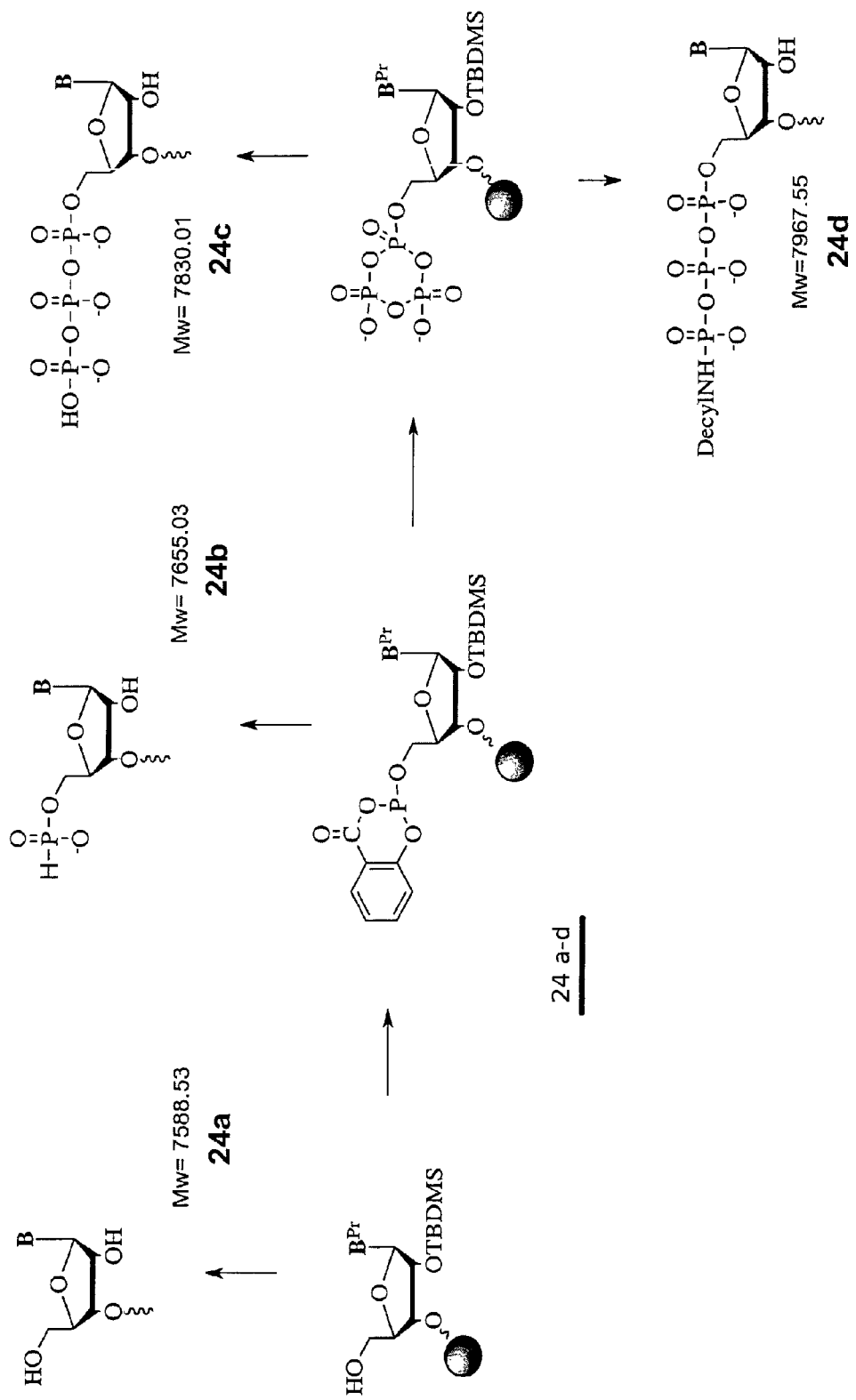
Figure 4B:
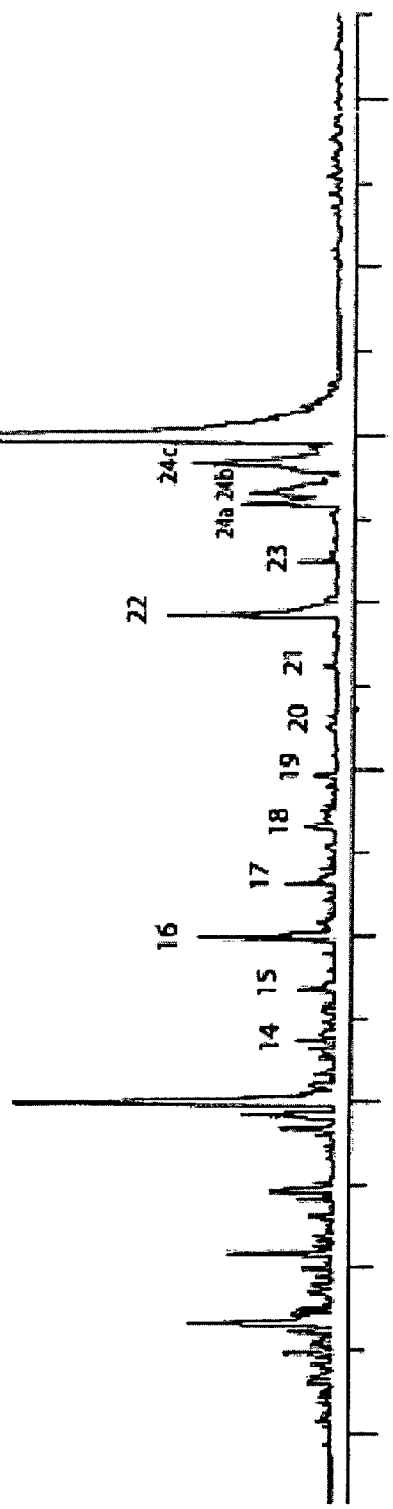

Preparation of a 5'-Triphosphate Modified Oligonucleotide Using a Decyl Amine Capture Tag Purification Step An overview of the reaction scheme described in Example 1 is shown in FIG. 1.

Step 1: Dissolve 203 mg (1 mmol) of 2-chloro-4H-1,3,2-benzodioxaphosphorin-4-one in 1 mL of dry dioxane in a 10 mL septum vial under argon.

Step 2: Dry the synthesis column containing the fully protected RNA that has been detritylated and thoroughly washed with acetonitrile, in vacuum for 12 h. Wash the column contents thoroughly by repeatedly drawing in and expelling 2 mL of anhydrous dioxane/pyridine solution, 3:1 (v/v) in an argon atmosphere.

Step 3: Add into a vial first 2 mL of pyridine/dioxane, 3:1 v/v followed by 100 µL of 1 M 2-chloro-4H-1,3,2-benzodioxaphosphorin-4-one solution in dry dioxane to give a 50 mM solution of the phosphitylating reagent, e.g. 2-chloro-4H-1,3,2-benzodioxaphosphorin-2-one, in dioxane/pyridine, 3:1 (v/v). Homogenize the solution by gently shaking. Start the reaction by drawing the 2-chloro-4H-1,3,2-benzodioxaphosphorin-4-one solution through the synthesis column from the vial.

During the reaction, repeatedly draw in and expel the 2-chloro-4H-1,3,2-benzodioxaphosphorin-4-one containing solution from the synthesis column, in order to allow thorough contact and good mixing with the solid phase supported RNA. A 30 min reaction time usually gives near quantitative reaction of the free 5'-OH group of the support bound oligomer in the 20-40 nt range.

Step 4: After a 30 min reaction time expel the dioxane/pyridine solution containing the excess phosphitylating agent into a waste container, fill a new syringe with a vortexed mixture of 1 mL of 0.5 M $(Bu_3NH)_2$ pyrophosphate in dry DMF and 238 μL (1 mmol) of dry $Bu_3N$ to give a 0.5 M $(Bu_3N)_4$ pyrophosphate solution. Push this solution through the column thereby replacing the dioxane/pyridine solution. The large excess of the pyrophosphate ensures a quantitative conversion of the intermediate to the P(III)—P(V) cyclic anhydride IIa.

Step 5: Wash the column with 3 mL of $CH_3CN$ to remove the DMF and excess $PP_i$, and to fill the column reactor with dry $CH_3CN$.

Step 6: Dissolve 300 μL of t-BuOOH (5.5 M solution in decane, Sigma-Aldrich) in 2 mL of anhydrous $CH_3CN$ to give an approximately 0.7 M homogeneous solution. Contact the synthesis support with this solution for 15 min in order to obtain the oxidized P(V) cyclic anhydride IIb.

Step 7: Wash the column with 3 mL of dry $CH_3CN$ to remove the excess peroxide and fill it with dry $CH_3CN$.

Step 8: Dissolve 300 μL of dry decylamine in 1 mL of dry $CH_3CN$ under argon and bring the solution in contact with the support in the column. Move the decylamine solution through the support. The contact time of the CPG with the amine solution should be 3 min.

Step 9: Wash the column thoroughly with 9 mL acetonitrile, then dry the column contents by flushing argon through it.

Step 10—First stage of the deprotection: Pass 1 mL of deprotection solution (40% aq. methylamine/conc. aq. ammonia 1:1 v/v. AMA reagent) through the support for 2-3 times. After a contact of 30 min transfer the solution into a new vial. Wash the support with same volume of AMA deprotection solution and combine the washings. Heat the combined solution and washings for 10 min at 65° C. After cooling on ice, concentrate the solution to a volume of 300-500 μL, then evaporate to dryness.

Step 11—Removal of the 2'-O-TBDMS protecting groups: Dry the residue by addition and coevaporation of 300 μL of dry EtOH, add 1 mL of dry 1 M TBAF (tetra-n-butylammonium fluoride) in THF, seal tightly and put on a shaker for 16 h. Quench the reaction with 1 mL of sterile aqueous 1 M TEAB (triethylammonium bicarbonate), and desalt it on a NAP™-25 (Nucleic Acid Purification) column using sterile water as eluent. Filtration through a sterile 2 μm filter may be necessary at this step. Combine and evaporate the UV-absorbing fractions to a volume of 150 μL, add 100 mL of 1 M TEAB pH8 and store the solution frozen at −20° C. until the HPLC purification can be performed. The decyl-NHpppRNA product is stable at −20° C. for weeks at pH 7-8.

Figure 7A:
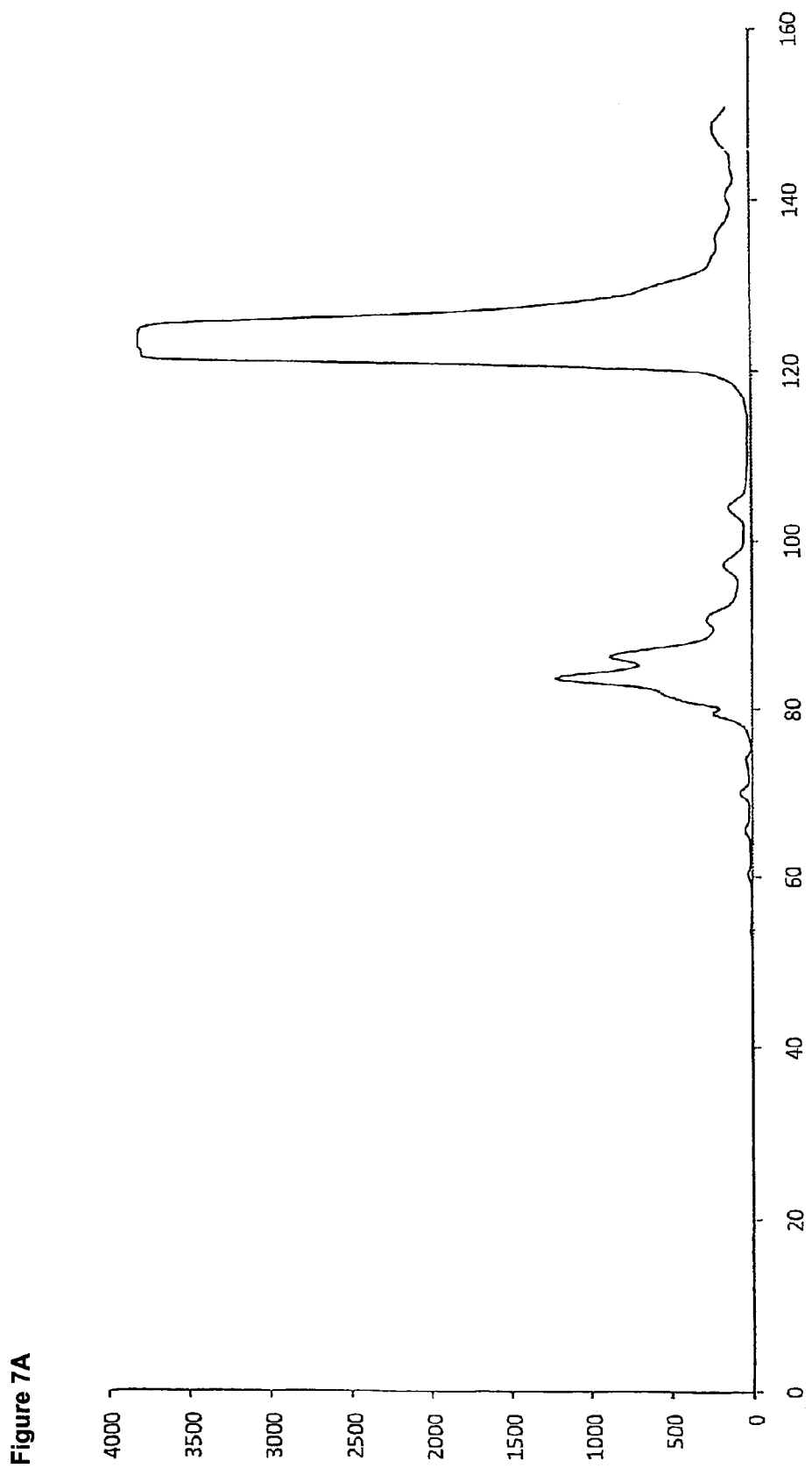
Figure 7B:
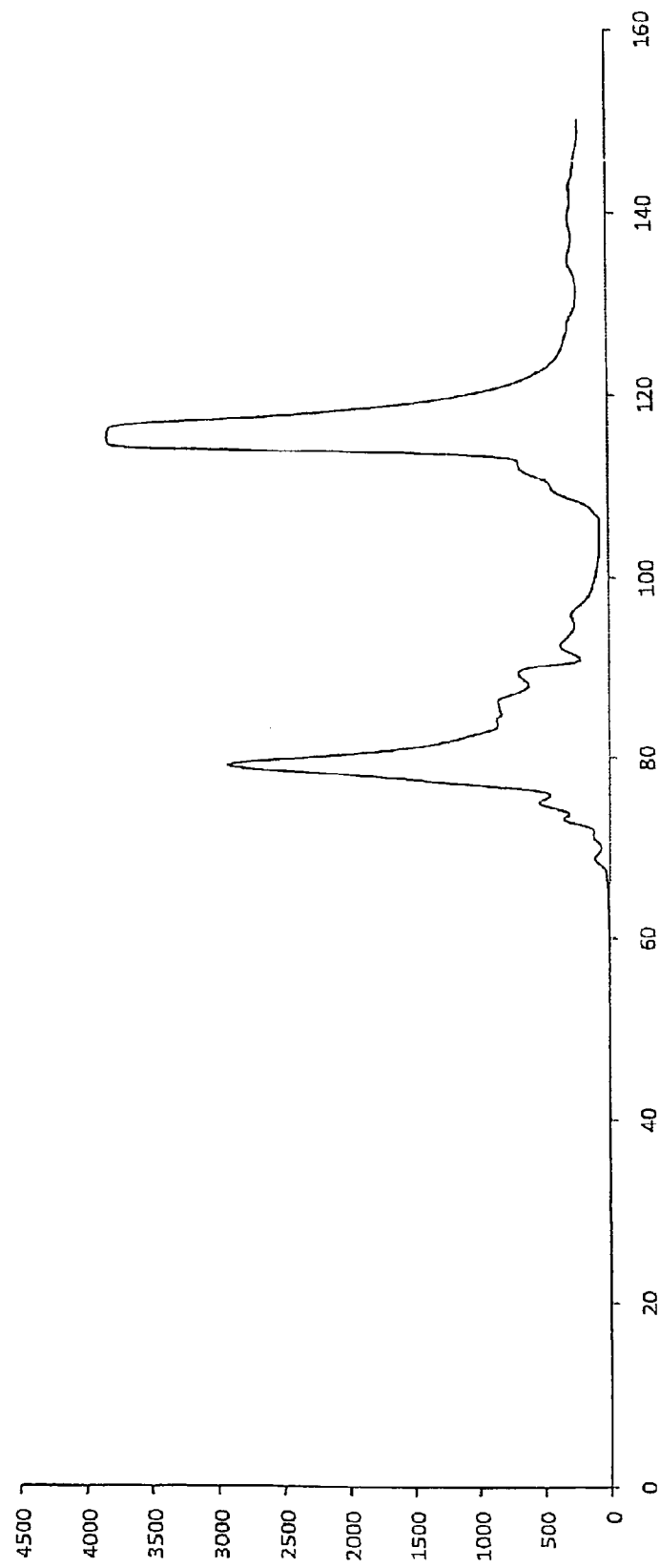
Figure 7C:
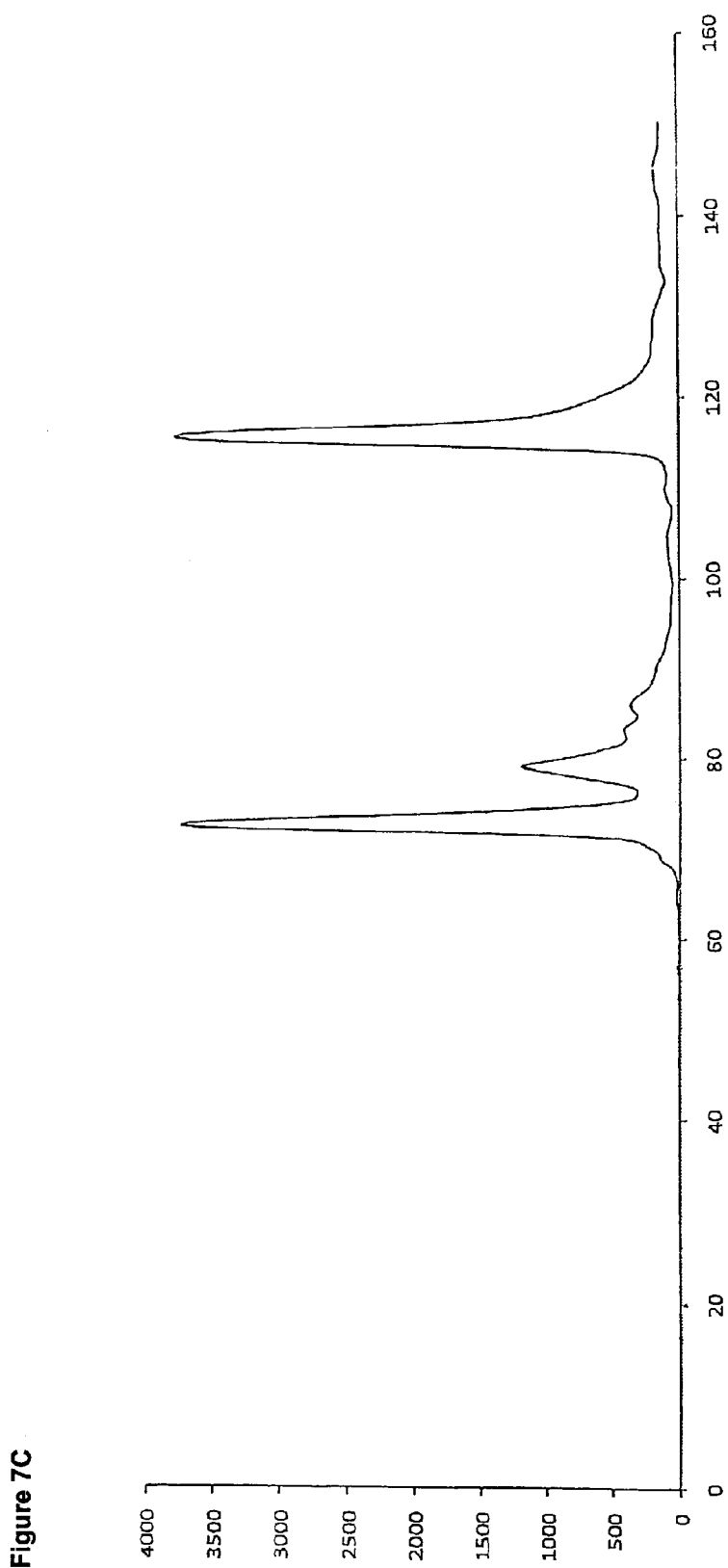
Figure 8:
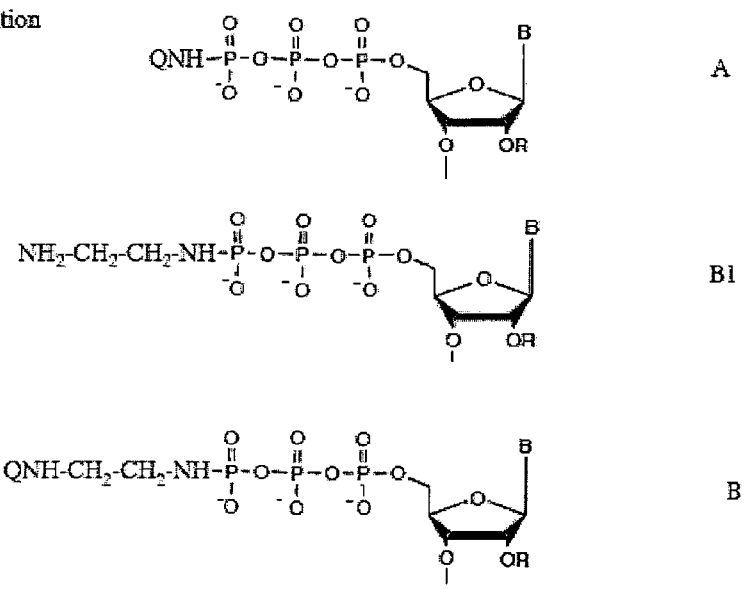
FIG. 8 shows especially preferred modified oligonucleotides of formula (I).
Figure 8:
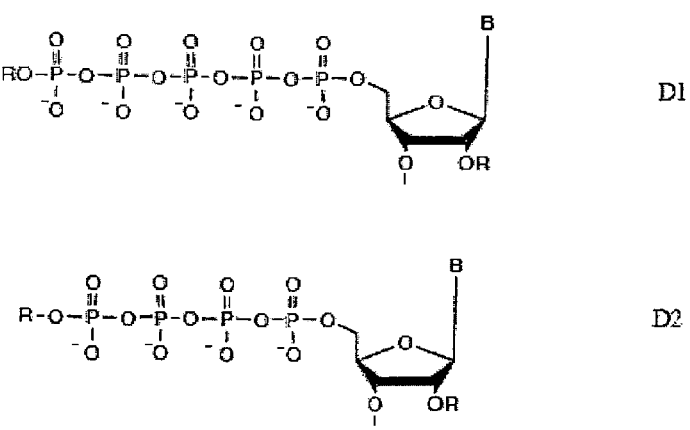

Step 12—HPLC purification: The reaction product from an 1 μmol scale reaction mixture from step 11 was loaded into a 7×25 mm PRP-1 column (Hamilton). Purification was performed using a linear gradient buffer B from 0 to 80% in 50 min at a flow rate of 3 mL/min. Buffer A is 100 mM TEAB and buffer B is 100 mM TEAB in methanol/water 8:2 v/v. A typical example of a 27-mer purification is shown in FIG. 7A.

Fractions 5 and 6 are collected, evaporated on a rotary evaporator and desalted by several coevaporations with dry methanol, The residue (approx. 200-250 nmol of decyl-NHpppRNA) was dissolved in water and transferred into a screw cap Eppendorf vial.

Step 13—Removal of the decylamine tag: 100 nmol of decyl-NHpppRNA was dissolved in 400 μL of pH 3.8 deprotection buffer in a 2 mL Eppendorf tube, and the sealed tube was heated at 60° C. for 70 min. These conditions result in quantitative cleavage of the phosphoramidate bond with no degradation of the triphosphate moiety. Then the reaction mixture was cooled on ice and 25 μL of sterile 5 M NaCl solution and 1.2 mL of absolute EtOH were added. After thorough mixing the solution was kept at −20° C. overnight to precipitate the pppRNA. The precipitate was collected by centrifugation, washed with cold ethanol, dried on a Speed-Vac, then dissolved in 500 mL of sterile water and stored frozen at −20° C.

TABLE 1

Summary of the reaction conditions for introduction of the 5'-terminal decyl-NHppp-residue.

| Step | Reagent | Time | |
|---|---|---|---|
| 1 | 3 mL dioxane/pyridine, 3:1 v/v | wash | → |
| 2 | 50 mM 2-chloro-4H-1,3,2-benzodioxaphosphorin-4-one in 2 mL of dioxane/pyridine, 3:1 v/v | 30 min | ←→ |
| 3 | 1 mL of 0.5M $(Bu_3NH)_2PP_i$ in DMF plus 238 μL of $Bu_3N$ | 10 min | ←→ |
| 4 | 3 mL of dry acetonitrile | wash | → |
| 5 | 300 μL of t-BuOOH (5.5M in decane) in 2 mL of $CH_3CN$ | 15 min | ←→ |
| 6 | 3 mL of dry acetonitrile | Wash | → |
| 7 | 300 μL of n-decylamine in 1 mL of dry acetonitrile (1.1M decylamine) | 3 min | ←→ |
| 8 | 10 mL of acetonitrile | wash | → |

1 μmol scale synthesis column containing support bound detritylated RNA
↔ bidirectional movements of reagents,
→ unidirectional washing step In analogous manner, a 5'-triphosphate modified oligonucleotide was also synthesized and purified using an octadecyl or a cholesteryl capture tag.

Example 2

Preparation of Triphosphate Oligonucleotides Using Non-Lipophilic Capture Tags (F-TAG-pppRNA and $N_3$-TAG-pppRNA)

Figure 9A:
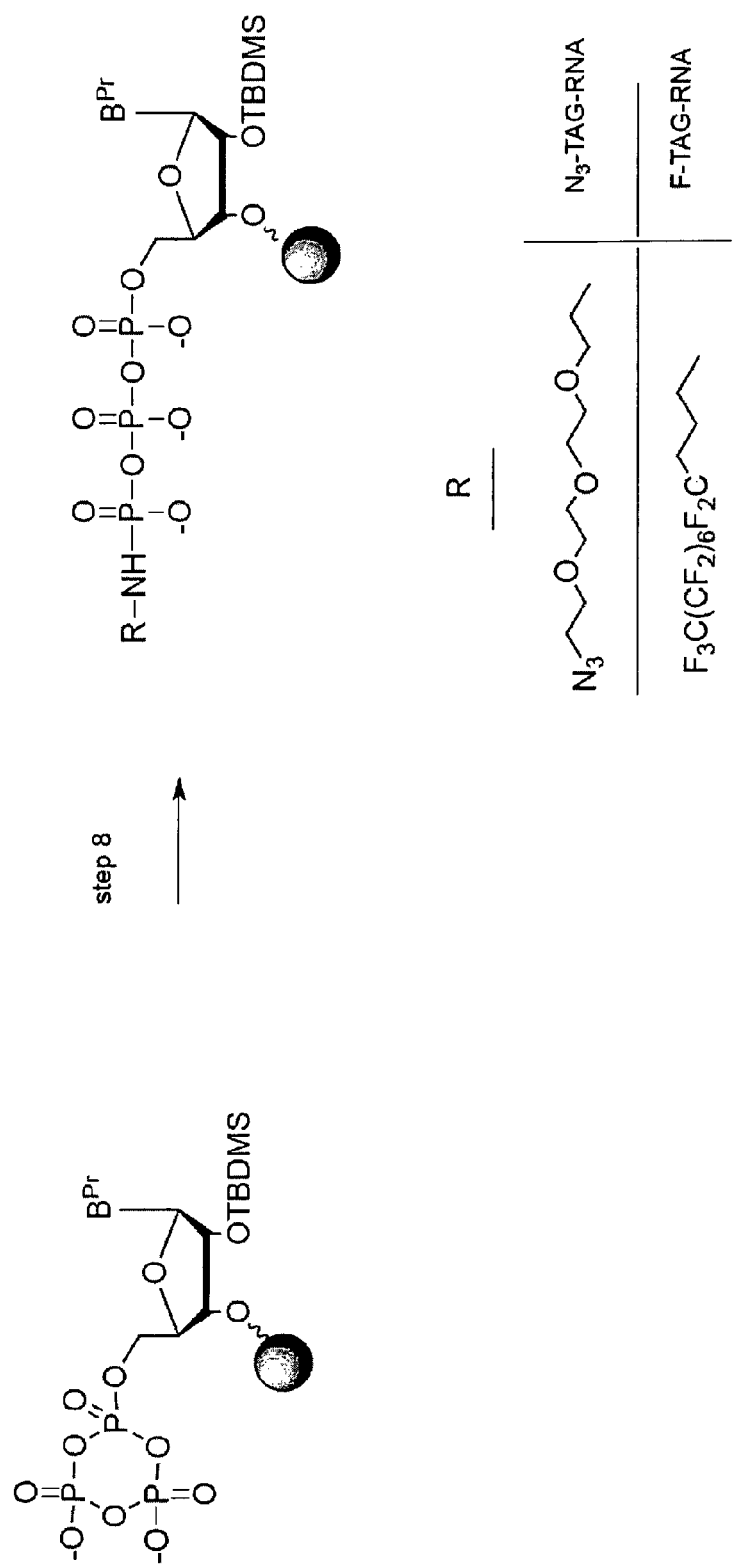
FIG. 9 shows the synthesis of compounds F-TAG-pppRNA and N3-TAG-pppRNA (A) and the strategy for reversible covalent immobilisation using N3-TAG RNA (B)
Figure 9B:
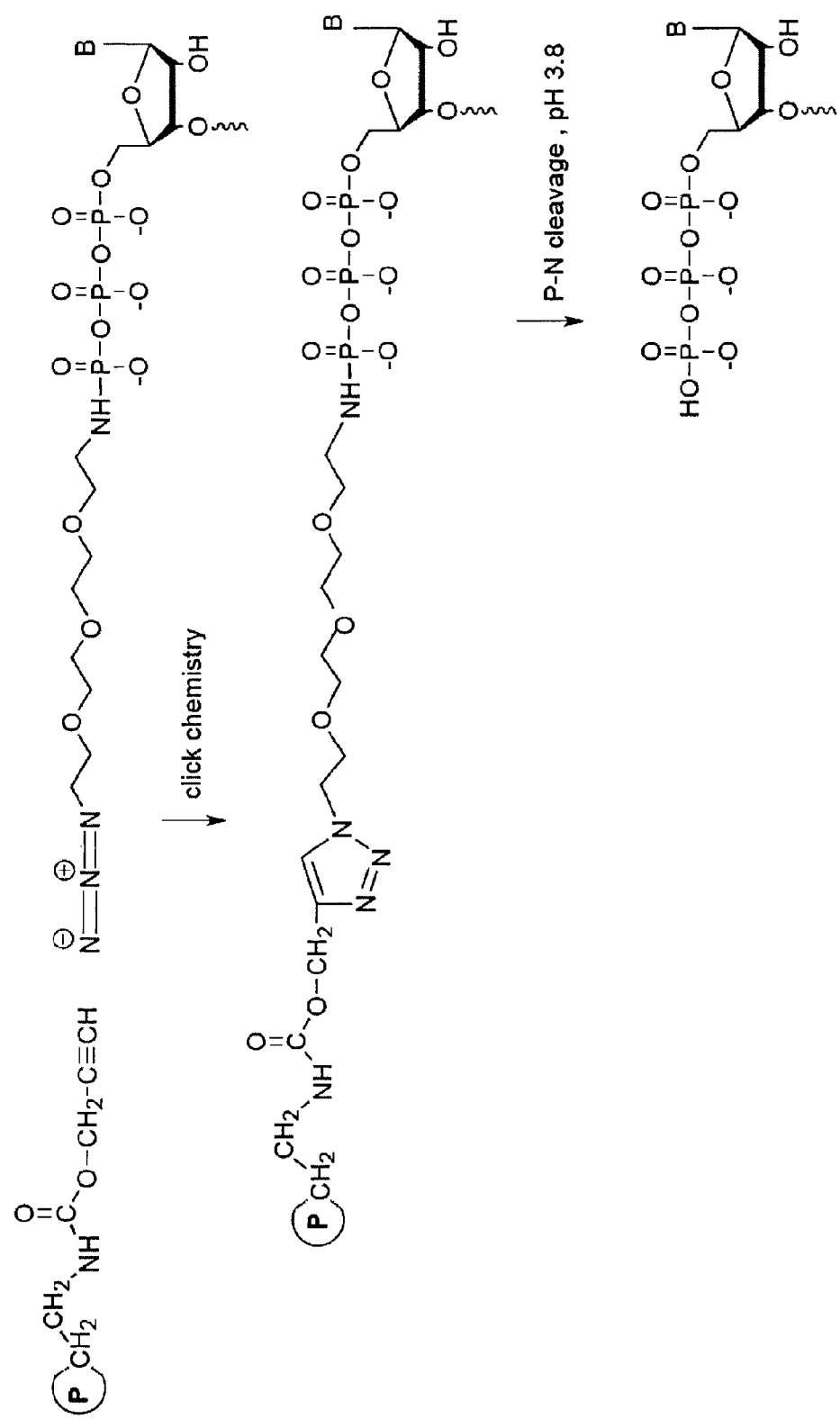

In order to demonstrate the utility of non-lipophilic interaction based purification strategies the pppRNA derivatives F-TAG-RNA and N3-TAG-RNA were prepared (see FIG. 9). All steps of the synthesis are identical with the procedure described in Example 1 except that in step 8 of FIG. 1, 2 mL of a 0.1 M solution of 4,4,5,5,6,6,7,7,8,8,9,9,10,10,11,11,11-Heptadecafluoroundecylamine in anhydrous acetonitrile was used for the ring opening of the solid phase bound cyclotriphosphate with an increased 3 h reaction time to give F-TAG-RNA; and 2 mL of a 0.1 M solution of 11-azido-3,6,9-trioxaundecan-1-amine in dry acetonitrile for 3 h was used to give $N_3$-TAG-pppRNA. The following deprotection steps are identical with those given in the detailed description for Dec-NHpppRNA in Example 1.

Figure 10A:
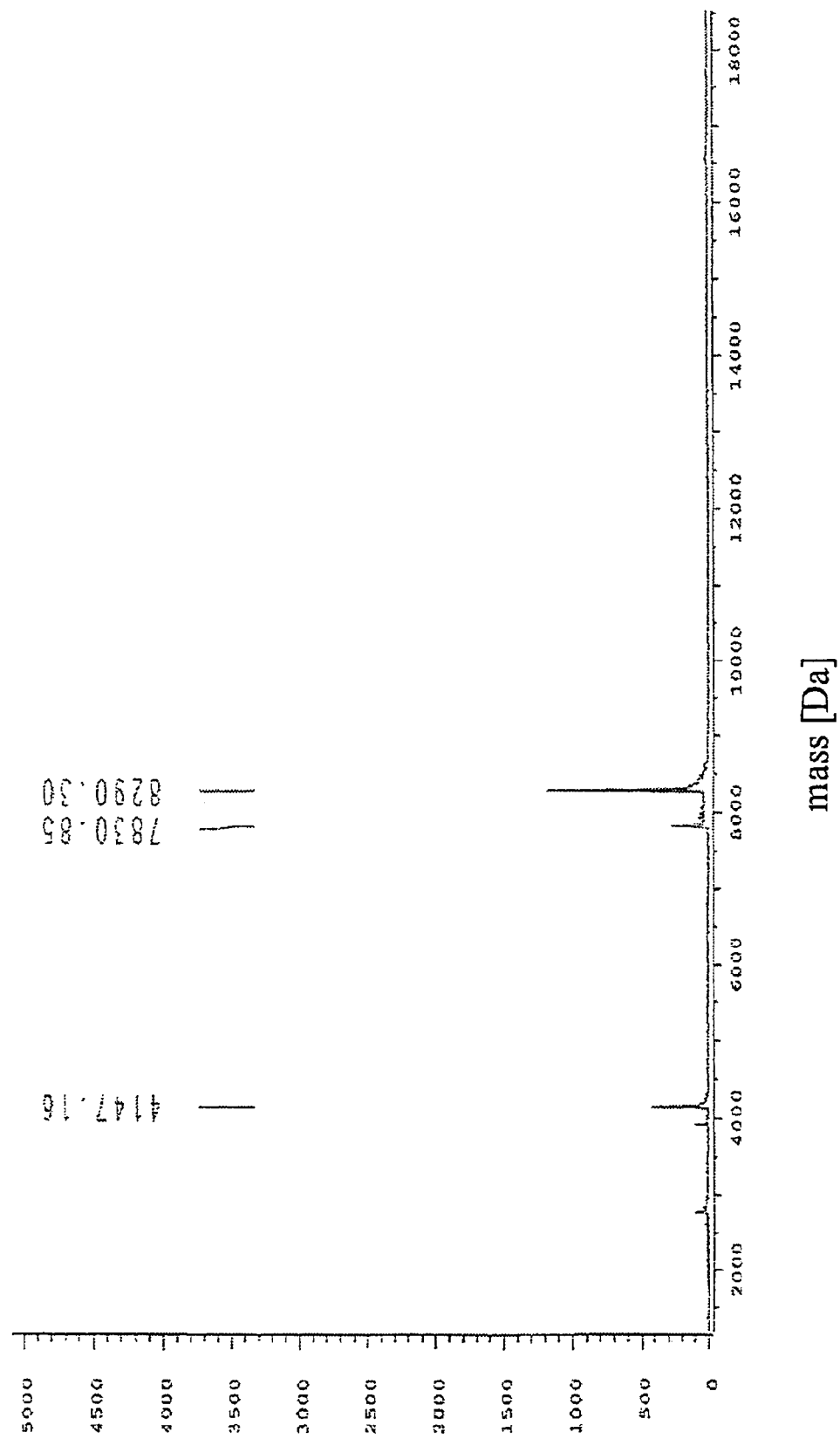
FIG. 10 shows MALDI spectra of F-TAG-pppRNA (A) N3-TAG-pppRNA (B)
Figure 10B:
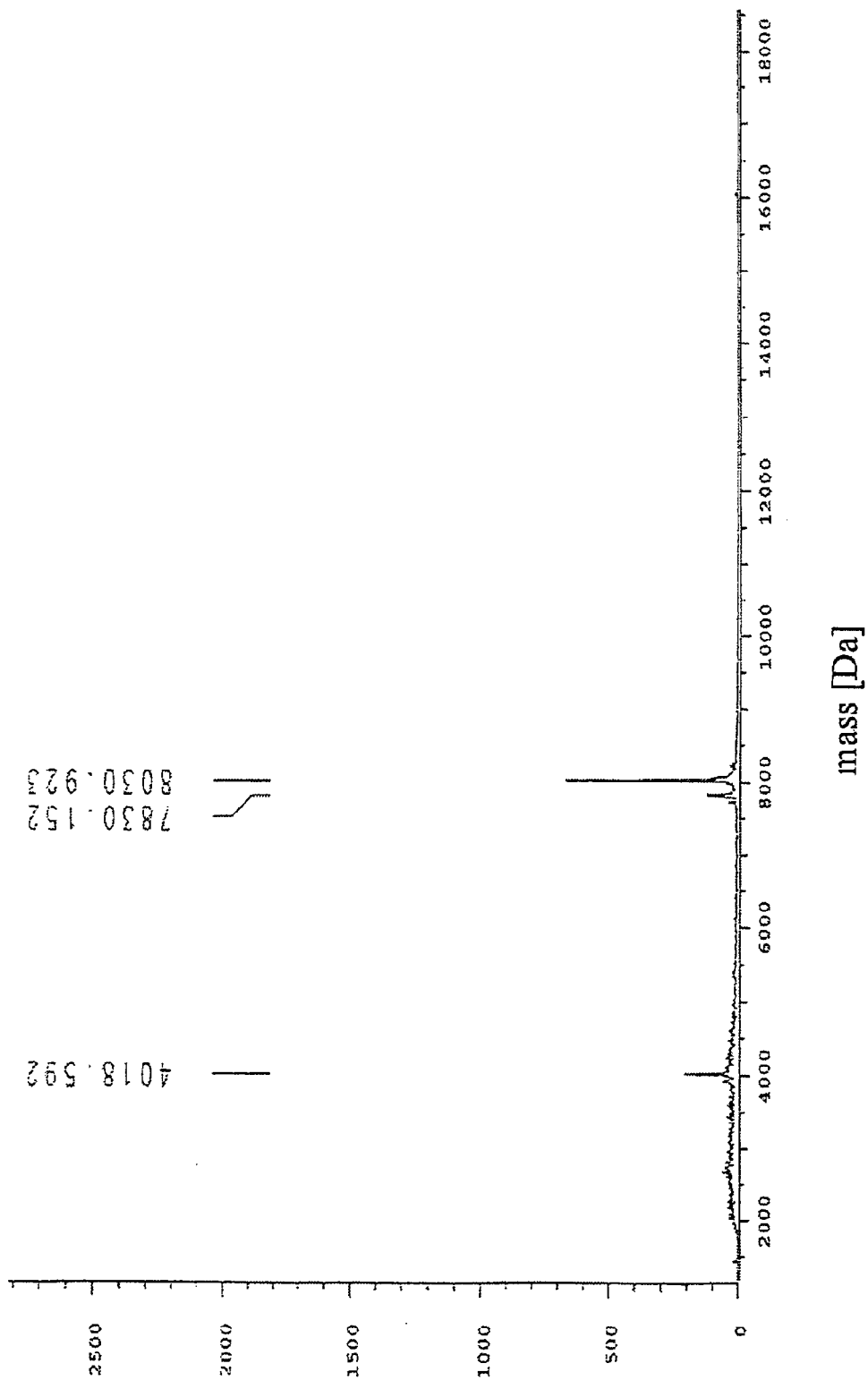

F-TAG-RNA and N3-TAG-RNA analytical data (see FIG. 10): (the RNA sequence in these examples is 5'-GACGCUGACCCUGAAGUUCAUCUU)

| | HPLC retention time* | Calculated Mass, Da | Mass measured by MALDI, Da | Time required for complete P—N cleavage at pH 3.8 at 60° C. |
|---|---|---|---|---|
| F-TAG-pppRNA | 15.1 min | 8287.74 | 8290.30 | 70 min |
| N3-TAG-pppRNA | 11 min | 8033.20 | 8033.92 | 70 min |

*PRP-1 column 0-100% B in 20 min (A = 100 mM Triethyammoniumbicarbonate (TEAB), B = 100 mM TEAB 80% MeOH)

pppRNA oligonucleotides containing fluorous tags (F-TAG-pppRNA) can be purified using commercial "fluorous" cartridges, or fluorous HPLC columns which enable the exploitation of the strong nonconvalent interaction between perfluorinated alkyl chains. The gamma azide modified pppRNA derivatives (N3-TAG-pppRNA) can be covalently bound to commercially available propyne modified solid phases by RNA compatible versions of the copper(I)-catalysed-alkyne-azide cycloaddition reaction (click chemistry). This procedure enables the purification of highly structured pppRNA sequences because in the resin bound form denaturing conditions can be applied to remove non-triphosphorylated by-products.

Figure 5:
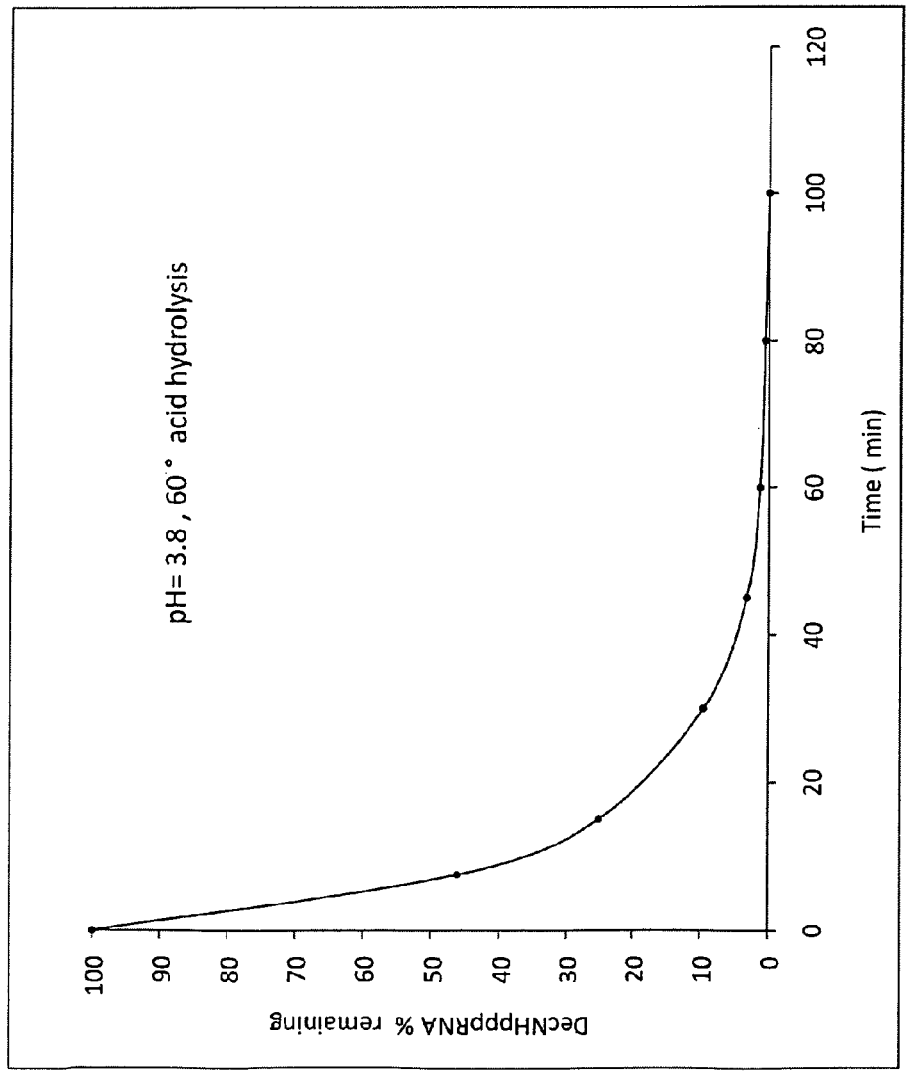
Figure 6A:
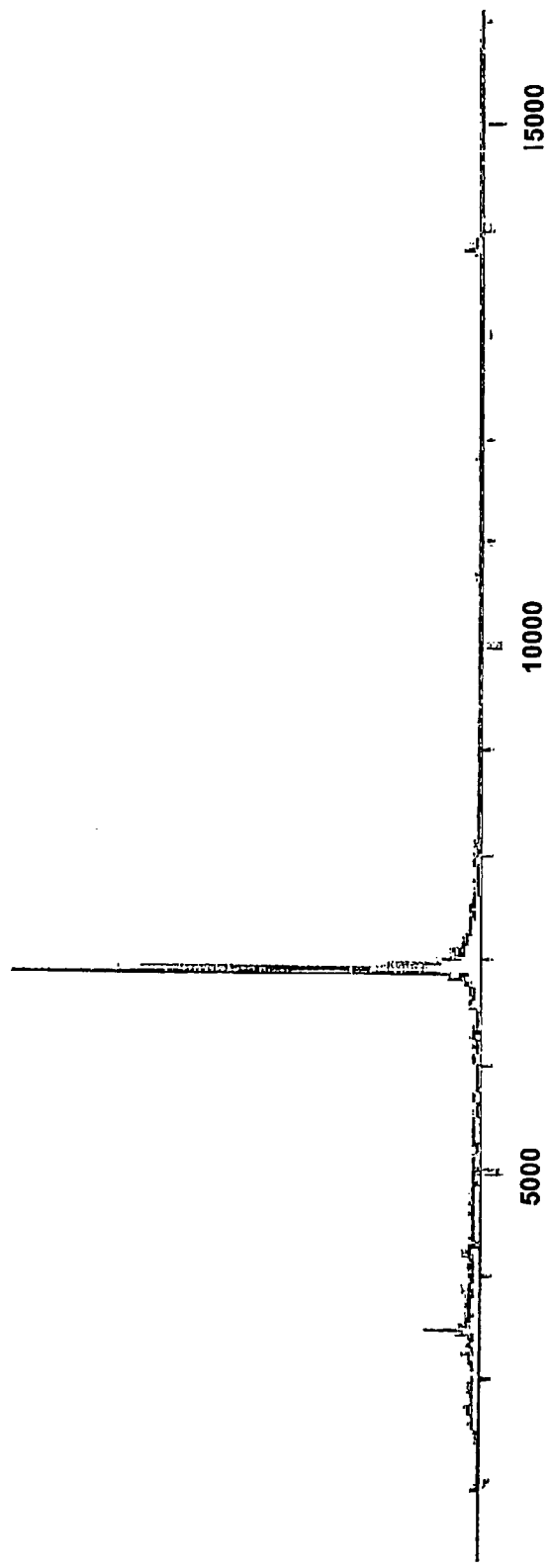
Figure 6B:
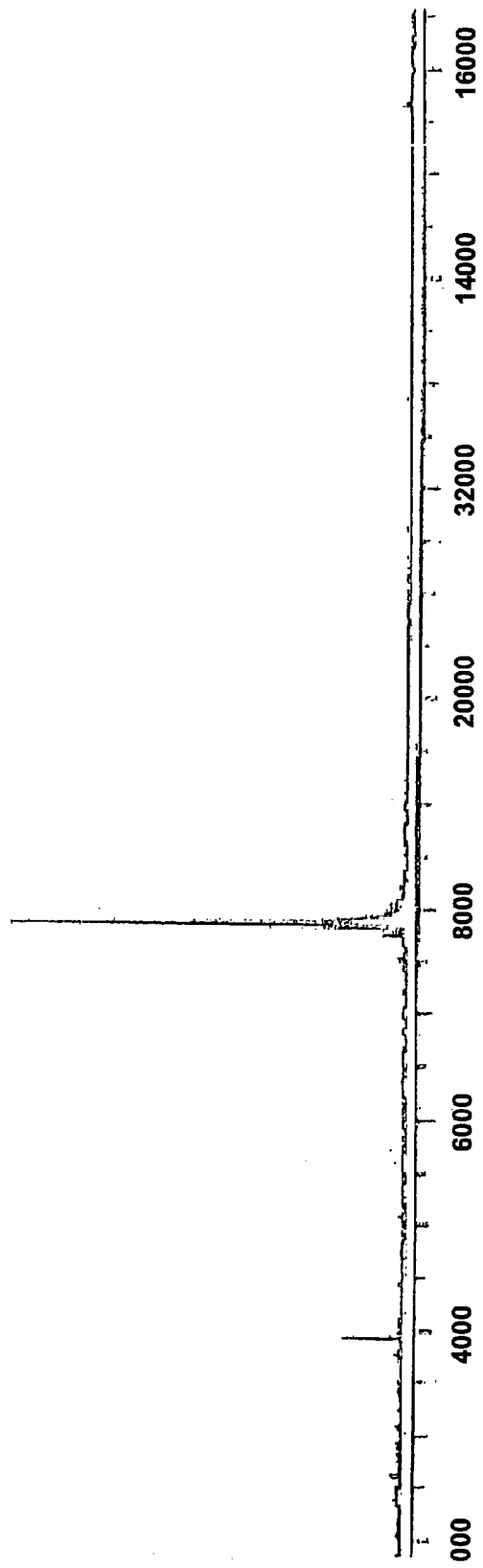
Figure 6C:
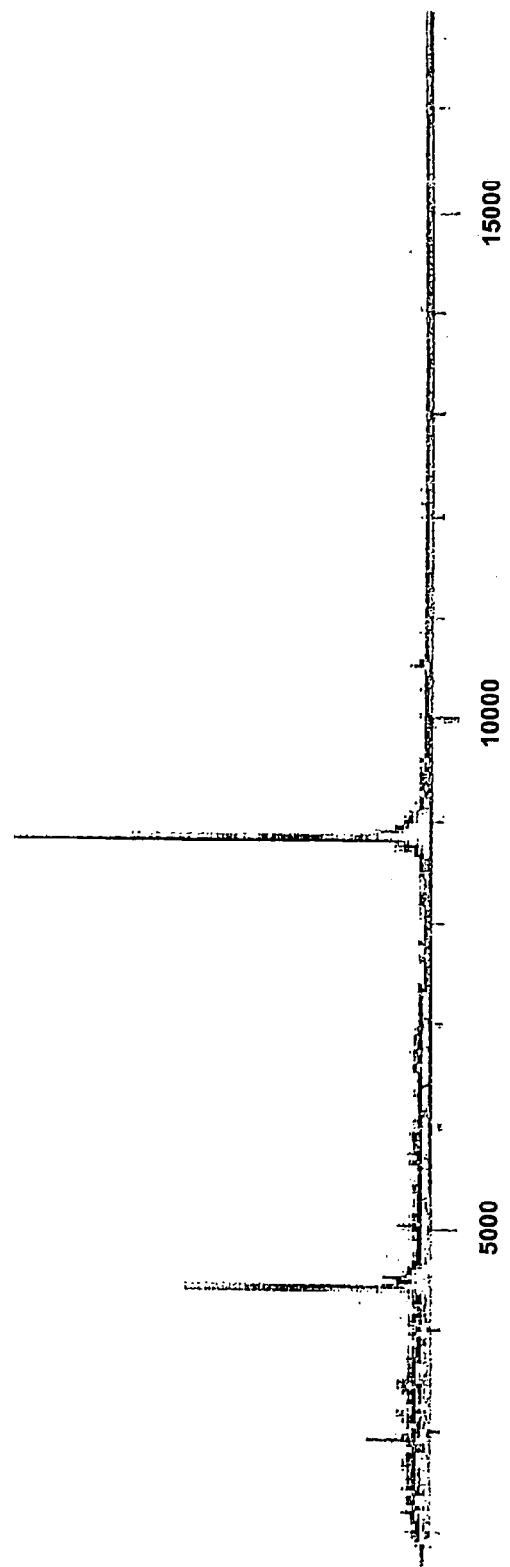

Upon acid hydrolysis both F-TAG-RNA and N3-TAG-RNA release the pppRNA end product with comparable kinetics to the simple P—N alkyl amide as described in FIG. 5.

Example 3

Variation of the RP-HPLC elution Position of Tag-pppRNA by n-alkyl Capture Tags of Increasing Chain Length Besides the n-decyl-tag described in Example 1, aliphatic n-alkyl residues with longer chain lengths ($C_{12}$, $C_{14}$, $C_{18}$) can be used to increase the retention time of the Tag-pppRNA product during RP-HPLC purification enabling an efficient separation from impurities that do not contain the tag.

N-dodecyl-NH-pppRNA, n-tetradecyl-NH-pppRNA and n-octadecyl-NH-pppRNA can be prepared following the procedure described in example 1 by variation of step 8: A 0.1 M solution of n-alkylamine (n-dodecylamine, n-tetradecylamine or n-octadecylamine) in dry $CH_2Cl_2$ is prepared and 2 mL of the solution is brought in contact with the support in the column. The alkylamine solution is pushed to and fro through the support. After a contact time of 3 h an additional washing step with 2 mL of $CH_2Cl_2$ is required prior to continuing with the next workup steps.

Analytical Data:

| | RP-HPLC* retention time (min) | Calculated Mass (Da) | Mass measured by MALDI (Da) | Time for complete P—N cleavage at pH 3.8 at 60° C. |
|---|---|---|---|---|
| $C_{12}$-NH-pppRNA | 15.5 | 7995.7 | 7999.2 | 70 min |
| $C_{14}$-NH-pppRNA | 17.3 | 8023.7 | 8028.1 | 70 min |
| $C_{18}$-NH-pppRNA | 19.7 | 8079.8 | 8082.2 | 70 min gives >80% product |

*PRP-1 column 0-100% B in 20 min (A = 100 mM Triethylammoniumbicarbonate, B = 100 mM TEAB 80% MeOH)

Figure 11:
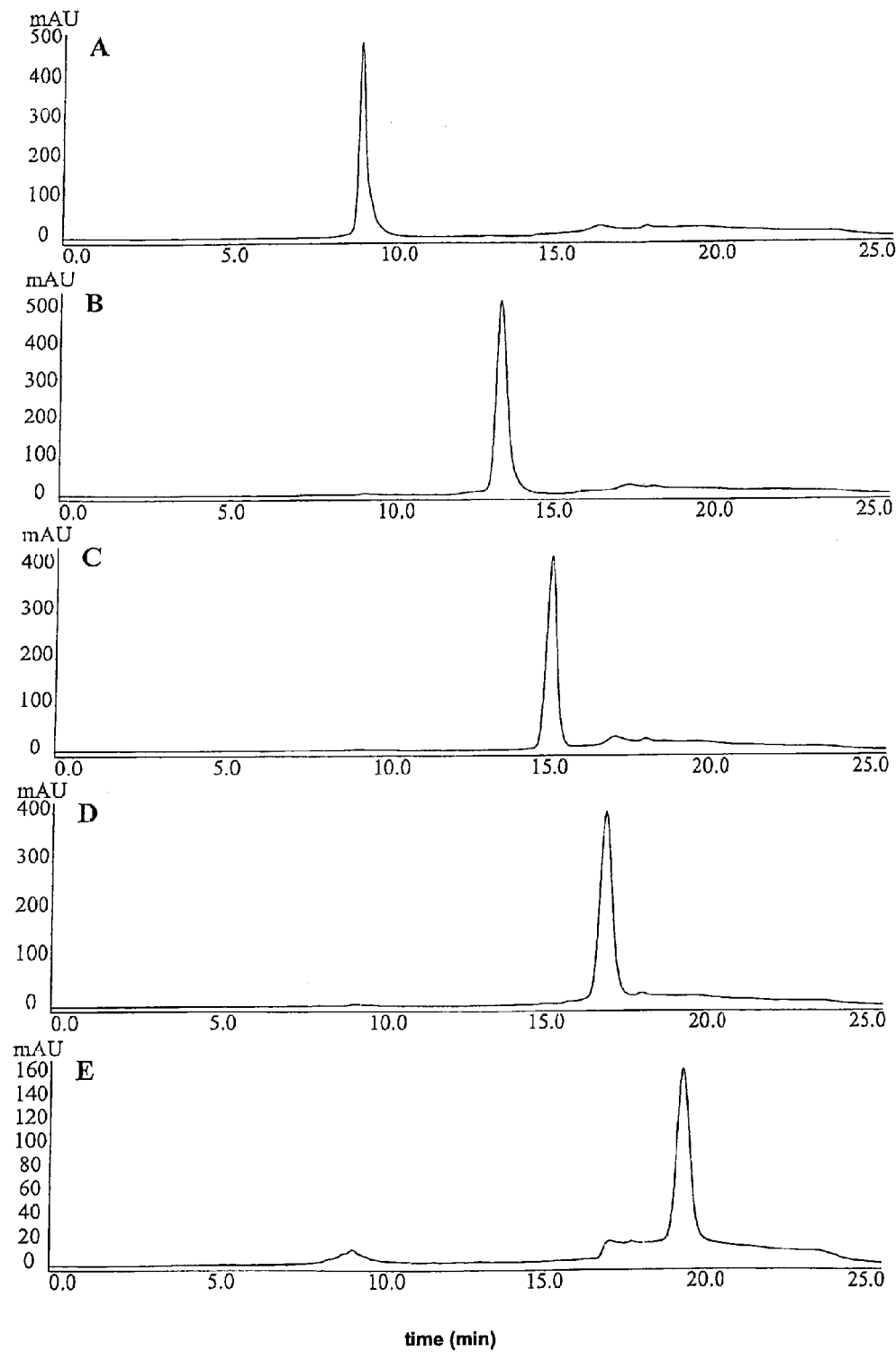
FIG. 11 shows the RP-HPLC analysis of pppRNA and n-alkyl-NH-pppRNAs with alkyl residues of increasing chain length.

FIG. 11 shows the RP-HPLC analysis of pppRNA and n-alkyl-NH-pppRNAs with alkyl residues of increasing chain length.

The invention claimed is:

1. A method of preparing an oligonucleotide of formula (I),

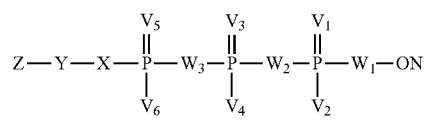

wherein $V_1$, $V_3$ and $V_5$ are independently in each case selected from O, S and Se;

$V_2$, $V_4$ and $V_6$ are independently in each case selected from OH, $OR^1$, SH, $SR^1$, F, $NH_2$, $NHR^1$, $N(R^1)_2$ and $BH_3^- M^+$, $W_1$ is O or S, $W_2$ is O, S, NH or $NR^2$, $W_3$ is O, S, NH, $NR^2$, $CH_2$, CHHal or $C(Hal)_2$, $R^1$, $R^2$ and $R^3$ are selected from $C_{1-6}$ alkyl, $C_{2-6}$ alkenyl, $C_{2-6}$ alkynyl, $C_{2-6}$ acyl or a cyclic group, each substituted or unsubstituted, or wherein two $R^1$ may form a ring together with an N-atom bound thereto, $M^+$ is a cation, X is NH, $NR^3$, O or S, Z represents a capture tag which is a long-chain alkyl residue, a perfluoroalkyl entity, an azide or an alkynyl group, Y represents a bond or a linker connecting the capture tag to X, and ON represents an oligonucleotide comprising at least 4 nucleotide or nucleotide analogue building blocks, comprising the steps:

(a) reacting a compound of formula (IIa)

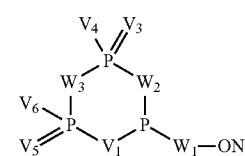

with an oxidizing agent to obtain a compound of formula (IIb)

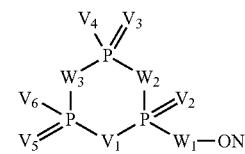

(b) reacting a compound of formula (IIb) with a capture tag agent of formula (III),

Z—Y—XH  (III)

to obtain a reaction product comprising the oligonucleotide of formula (I), and (c) contacting the reaction product of step (b) with a capture reagent capable of interacting with the capture tag, wherein the contacting takes place under conditions which allow separation of the oligonucleotide (I) from other species contained in said reaction product.

2. The method of claim 1, wherein the capture tag and the capture reagent capable of interacting therewith are selected from:

(i) a hydrophobic or fluorinated group and a chromatographic material with affinity for hydrophobic or fluorinated groups;

(ii) a first partner of a non-covalent binding pair and a second partner of a non-covalent binding pair, and (iii) a first partner of a covalent binding pair and a second partner of a covalent binding pair, where the first and second partner form covalent bonds.

3. The method of claim 1,
wherein the triphosphate/triphosphate analogue group is attached to the 5'-terminus of the oligonucleotide.

4. The method of claim 1, further comprising the step:

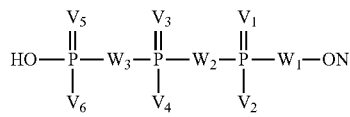

IV (d) removing the capture tag to obtain an oligonucleotide of formula (IV):
wherein $V_1$, $V_3$, $V_5$, $V_2$, $V_4$, $V_6$, $W_1$, $W_2$, $W_3$ and ON are as defined in claim 1.

5. The method of claim 1, wherein the oligonucleotide is selected from desoxyribonucleotides, ribonucleotides and oligonucleotide analogues.

6. The method of claim 1, wherein the oligonucleotide is single-stranded or double stranded.

7. The method of claim 6, wherein the oligonucleotide is double-stranded and the duplex is closed by a loop at the distal end thereof, wherein the loop comprises nucleotide and/or non-nucleotide building blocks.

8. The method of claim 6, wherein the oligonucleotide is double-stranded and the duplex is blunt-ended at the proximal end thereof.

9. The method of claim 1, wherein the oligonucleotide comprises a cell-specific targeting entity covalently attached thereto.

10. The method of claim 1, wherein the oligonucleotide of formula (I) or an oligonucleotide of formula (IV)

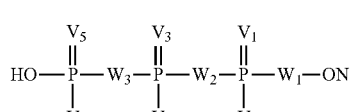

IV wherein $V_1$, $V_3$, $V_5$, $V_2$, $V_4$, $V_6$, $W_1$, $W_2$, $W_3$ and ON are as defined in claim 1, is an activator of RIG-1.

11. Oligonucleotide of Formula (I), obtainable by a method comprising (a) reacting a compound of formula (IIa)

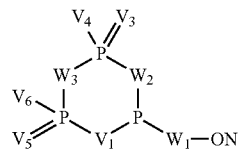

IIa with an oxidizing agent to obtain a compound of formula (IIb)

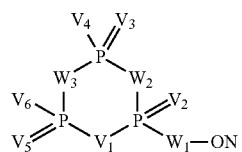

IIb (b) reacting a compound of formula (IIb) with a capture tag agent of formula (III), $$Z-Y-XH \qquad (III)$$

to obtain a reaction product comprising the oligonucleotide of formula (I), and (c) contacting the reaction product of step (b) with a capture reagent capable of interacting with the capture tag, wherein the contacting takes place under conditions which allow separation of the oligonucleotide (I) from other species contained in said reaction product, wherein $V_1$, $V_3$ and $V_5$ are independently in each case selected from O, S and Se;

$V_2$, $V_4$ and $V_6$ are independently in each case selected from OH, $OR^1$, SH, $SR^1$, F, $NH_2$, $NHR^1$, $N(R^1)_2$ and $BH_3^- M^+$, $W_1$ is O or S, $W_2$ is O, S, NH or $NR^2$, $W_3$ is O, S, NH, $NR^2$, $CH_2$, CHHal or $C(Hal)_2$, $R^1$, $R^2$ and $R^3$ are selected from $C_{1-6}$ alkyl, $C_{2-6}$ alkenyl, $C_{2-6}$ alkynyl, $C_{2-6}$ acyl or a cyclic group, each substituted or unsubstituted, or wherein two $R^1$ may form a ring together with an N-atom bound thereto, $M^+$ is a cation, X is NH, $NR^3$, O or S, Z represents a capture tag which is a long-chain alkyl residue, a perfluoroalkyl entity, an azide or an alkynyl group, Y represents a bond or a linker connecting the capture tag to X, and ON represents an oligonucleotide comprising at least 4 nucleotide or nucleotide analogue building blocks.

12. A kit for preparing an oligonucleotide of formula (I)

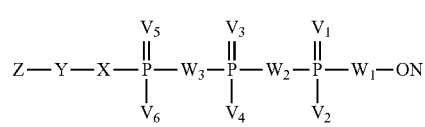

I wherein $V_1$, $V_3$, $V_5$, $V_2$, $V_4$, $V_6$, $W_1$, $W_2$, $W_3$, X, Y, Z and ON are defined as in claim 1, wherein the kit comprises:

(a) a capture tag agent of formula (III)

$$Z-Y-XH \quad (III)$$

wherein X, Z and Y are defined as in claim 1, and (b) a capture reagent capable of interacting with the capture tag.

13. A modified oligonucleotide of formula (I)

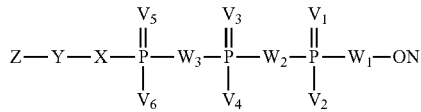

wherein

X is NH, O, $R-O-[P(V_1)V_2-W_1]_n$ or $R-O-P(V_3)V_4-W_2-P-(V_1)V_2-W_1$, n is 1-12,

Y is a bond,

Z is $C_{13}$-$C_{24}$ alkyl, Q or $QNHC_2$-$C_{24}$ alkyl,

Q is $C_1$-$C_{24}$ alkyl,

R is $C_1$-$C_{24}$ alkyl, $C_2$-$C_{24}$ alkenyl, $C_2$-$C_{24}$ alkynyl and lipids, or R is $C_1$-$C_{24}$ alkyl, $C_2$-$C_{24}$ alkenyl, $C_2$-$C_{24}$ alkynyl, $C_2$-$C_{24}$ acyl or a cyclic group, and is substituted or unsubstituted, and $V_1, V_2, V_3, V_4, V_5, V_6, W_1, W_2, W_3$ and ON are defined in claim 1.

14. The modified oligonucleotide of claim 13, wherein

X is NH or O, and

Z is selected from the group consisting of $C_{13}$-$C_{24}$ alkyl, Q and $QNHC_2$-$C_{24}$ alkyl.

15. The modified oligonucleotide of claim 13, wherein

X is $R-O-[P(V_1)V_2-W_1]_n$, n is 1 or 2, and $V_1, V_2$ and $W_1$ are O.

16. The method according to claim 2, wherein said chromatographic material with affinity for hydrophobic or fluorinated groups is a reversed phase material or a fluorous affinity support.

17. The method of claim 3, wherein the triphosphate/triphosphate analogue group is attached to the 5'-OH-group of the 5'-terminal sugar thereof.

18. The modified oligonucleotide according to claim 13, wherein n is 1 or 2, and $V_1, V_2, V_3, V_4, V_5, V_6, W_1, W_2$ and $W_3$ are O.

* * * * *